(12) United States Patent
Swayze

(10) Patent No.: US 8,540,131 B2
(45) Date of Patent: Sep. 24, 2013

(54) SURGICAL STAPLE CARTRIDGES WITH TISSUE TETHERS FOR MANIPULATING DIVIDED TISSUE AND METHODS OF USING SAME

(75) Inventor: Jeffrey S. Swayze, Hamilton, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 345 days.

(21) Appl. No.: 13/048,608

(22) Filed: Mar. 15, 2011

(65) Prior Publication Data

US 2012/0234900 A1 Sep. 20, 2012

(51) Int. Cl.
*A61B 17/068* (2006.01)

(52) U.S. Cl.
USPC ....... 227/176.1; 227/19; 227/180.1; 606/139; 606/151; 606/219

(58) Field of Classification Search
USPC ............... 227/19, 175.1, 176.1, 178.1, 180.1; 606/139, 143, 151, 153, 219
See application file for complete search history.

(56) References Cited

U.S. PATENT DOCUMENTS

| | | | |
|---|---|---|---|
| 5,702,409 A * | 12/1997 | Rayburn et al. | 606/151 |
| 5,810,855 A * | 9/1998 | Rayburn et al. | 606/151 |
| 5,865,361 A | 2/1999 | Milliman et al. | |
| 6,017,356 A | 1/2000 | Frederick et al. | |
| 7,000,818 B2 | 2/2006 | Shelton, IV et al. | |
| 7,328,828 B2 | 2/2008 | Ortiz et al. | |
| 7,354,447 B2 | 4/2008 | Shelton, IV et al. | |
| 7,407,078 B2 | 8/2008 | Shelton, IV et al. | |
| 7,416,101 B2 | 8/2008 | Shelton, IV et al. | |
| 7,422,139 B2 | 9/2008 | Shelton, IV et al. | |
| 7,431,189 B2 | 10/2008 | Shelton, IV et al. | |
| 7,434,717 B2 | 10/2008 | Shelton, IV et al. | |
| 7,438,209 B1 | 10/2008 | Hess et al. | |
| 7,441,684 B2 | 10/2008 | Shelton, IV et al. | |
| 7,441,685 B1 | 10/2008 | Boudreaux | |
| 7,448,525 B2 | 11/2008 | Shelton, IV et al. | |
| 7,464,846 B2 | 12/2008 | Shelton, IV et al. | |
| 7,464,849 B2 | 12/2008 | Shelton, IV et al. | |
| 7,467,740 B2 | 12/2008 | Shelton, IV et al. | |
| 7,472,815 B2 | 1/2009 | Shelton, IV et al. | |
| 7,490,749 B2 | 2/2009 | Schall et al. | |

(Continued)

FOREIGN PATENT DOCUMENTS

| CA | 2458946 A1 | 3/2003 |
|---|---|---|
| CA | 2512960 A1 | 1/2006 |

(Continued)

OTHER PUBLICATIONS

U.S. Appl. No. 13/048,559, filed Mar. 15, 2011.

(Continued)

*Primary Examiner* — Scott A. Smith

(57) ABSTRACT

Surgical staple cartridges and methods for manipulating the severed ends of divided tissue. In various forms, the staple cartridge has at least one base material temporarily supported thereon that is oriented to be stapled to a corresponding end of the divided tissue. At least one elongated tether is non-removably affixed to each piece of base material. Once the base material is stapled to the corresponding piece of divided tissue, the clinician may manipulate that pieced of divided tissue by applying manipulation motions to the tether. Corresponding grooves or pockets may be provided on the cartridge body for temporarily supporting the tethers therein.

8 Claims, 12 Drawing Sheets

(56) References Cited

U.S. PATENT DOCUMENTS

| | | |
|---|---|---|
| 7,500,979 B2 | 3/2009 | Hueil et al. |
| 7,506,791 B2 | 3/2009 | Omaits et al. |
| 7,510,107 B2 | 3/2009 | Timm et al. |
| 7,549,564 B2 | 6/2009 | Boudreaux |
| 7,568,603 B2 | 8/2009 | Shelton, IV et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,644,848 B2 | 1/2010 | Swayze et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,721,931 B2 | 5/2010 | Shelton, IV et al. |
| 7,721,934 B2 | 5/2010 | Shelton, IV et al. |
| 7,721,936 B2 | 5/2010 | Shelton, IV et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,612 B2 | 11/2010 | Baxter, III et al. |
| 7,837,080 B2 | 11/2010 | Schwemberger |
| 7,845,537 B2 | 12/2010 | Shelton, IV et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,913,891 B2 | 3/2011 | Doll et al. |
| 7,918,377 B2 | 4/2011 | Measamer et al. |
| 7,922,061 B2 | 4/2011 | Shelton, IV et al. |
| 7,934,630 B2 | 5/2011 | Shelton, IV et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,959,051 B2 | 6/2011 | Smith et al. |
| 7,966,799 B2 | 6/2011 | Morgan et al. |
| 7,980,443 B2 | 7/2011 | Scheib et al. |
| 7,992,757 B2 * | 8/2011 | Wheeler et al. ............ 227/176.1 |
| 8,011,550 B2 * | 9/2011 | Aranyi et al. ............. 227/175.1 |
| 8,011,555 B2 * | 9/2011 | Tarinelli et al. ........... 227/180.1 |
| 8,020,743 B2 | 9/2011 | Shelton, IV |
| 8,056,787 B2 | 11/2011 | Boudreaux et al. |
| 8,066,167 B2 | 11/2011 | Measamer et al. |
| D650,074 S | 12/2011 | Hunt et al. |
| 8,083,120 B2 | 12/2011 | Shelton, IV et al. |
| 8,231,043 B2 * | 7/2012 | Tarinelli et al. ........... 227/180.1 |
| 8,353,438 B2 * | 1/2013 | Baxter et al. ............... 227/176.1 |
| 2006/0011699 A1 | 1/2006 | Olson et al. |
| 2007/0102472 A1 | 5/2007 | Shelton, IV |
| 2007/0106317 A1 | 5/2007 | Shelton, IV et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0225562 A1 | 9/2007 | Spivey et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082125 A1 | 4/2008 | Murray et al. |
| 2008/0082126 A1 | 4/2008 | Murray et al. |
| 2008/0167522 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0296346 A1 | 12/2008 | Shelton, IV et al. |
| 2008/0300580 A1 | 12/2008 | Shelton, IV et al. |
| 2008/0308602 A1 | 12/2008 | Timm et al. |
| 2008/0308603 A1 | 12/2008 | Shelton, IV et al. |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0076534 A1 | 3/2009 | Shelton, IV et al. |
| 2009/0149871 A9 | 6/2009 | Kagan et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0209946 A1 | 8/2009 | Swayze et al. |
| 2009/0209990 A1 | 8/2009 | Yates et al. |
| 2009/0242610 A1 | 10/2009 | Shelton, IV et al. |
| 2010/0012704 A1 | 1/2010 | Tarinelli Racenet et al. |
| 2010/0032470 A1 | 2/2010 | Hess et al. |
| 2010/0069942 A1 | 3/2010 | Shelton, IV |
| 2010/0072254 A1 | 3/2010 | Aranyi et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0213241 A1 | 8/2010 | Bedi et al. |
| 2010/0222901 A1 | 9/2010 | Swayze et al. |

| | | | |
|---|---|---|---|
| 2010/0224669 A1 | 9/2010 | Shelton, IV et al. | |
| 2010/0243707 A1 | 9/2010 | Olson et al. | |
| 2010/0243708 A1 | 9/2010 | Aranyi et al. | |
| 2010/0243709 A1 | 9/2010 | Hess et al. | |
| 2010/0264193 A1 | 10/2010 | Huang et al. | |
| 2010/0264194 A1 | 10/2010 | Huang et al. | |
| 2010/0294829 A1 | 11/2010 | Giordano et al. | |
| 2010/0301095 A1 | 12/2010 | Shelton, IV et al. | |
| 2010/0301096 A1 | 12/2010 | Moore et al. | |
| 2010/0305552 A1 | 12/2010 | Shelton, IV et al. | |
| 2010/0308100 A1 | 12/2010 | Boudreaux | |
| 2011/0006099 A1 | 1/2011 | Hall et al. | |
| 2011/0006101 A1 | 1/2011 | Hall et al. | |
| 2011/0006103 A1 | 1/2011 | Laurent et al. | |
| 2011/0011914 A1 | 1/2011 | Baxter, III et al. | |
| 2011/0011915 A1 | 1/2011 | Shelton, IV | |
| 2011/0024477 A1 | 2/2011 | Hall et al. | |
| 2011/0024478 A1 | 2/2011 | Shelton, IV | |
| 2011/0024479 A1 | 2/2011 | Swensgard et al. | |
| 2011/0042441 A1 | 2/2011 | Shelton, IV et al. | |
| 2011/0060363 A1 | 3/2011 | Hess et al. | |
| 2011/0062212 A1 | 3/2011 | Shelton, IV et al. | |
| 2011/0068145 A1 | 3/2011 | Bedi et al. | |
| 2011/0068148 A1 | 3/2011 | Hall et al. | |
| 2011/0084113 A1 | 4/2011 | Bedi et al. | |
| 2011/0084115 A1 | 4/2011 | Bedi et al. | |
| 2011/0087276 A1 | 4/2011 | Bedi et al. | |
| 2011/0114697 A1 | 5/2011 | Baxter, III et al. | |
| 2011/0114698 A1 | 5/2011 | Baxter, III et al. | |
| 2011/0114699 A1 | 5/2011 | Baxter, III et al. | |
| 2011/0114700 A1 | 5/2011 | Baxter, III et al. | |
| 2011/0118761 A1 | 5/2011 | Baxter, III et al. | |
| 2011/0121051 A1 | 5/2011 | Shelton, IV et al. | |
| 2011/0121052 A1 | 5/2011 | Shelton, IV et al. | |
| 2011/0125176 A1 | 5/2011 | Yates et al. | |
| 2011/0125177 A1 | 5/2011 | Yates et al. | |
| 2011/0132962 A1 | 6/2011 | Hall et al. | |
| 2011/0132963 A1 | 6/2011 | Giordano et al. | |
| 2011/0132964 A1 | 6/2011 | Weisenburgh, II et al. | |
| 2011/0132965 A1 | 6/2011 | Moore et al. | |
| 2011/0139852 A1 | 6/2011 | Zingman | |
| 2011/0144430 A1 | 6/2011 | Spivey et al. | |
| 2011/0147433 A1 | 6/2011 | Shelton, IV et al. | |
| 2011/0147434 A1 | 6/2011 | Hueil et al. | |
| 2011/0155780 A1 | 6/2011 | Boudreaux | |
| 2011/0155781 A1 | 6/2011 | Swensgard et al. | |
| 2011/0155785 A1 | 6/2011 | Laurent et al. | |
| 2011/0155787 A1 | 6/2011 | Baxter, III et al. | |
| 2011/0163147 A1 | 7/2011 | Laurent et al. | |
| 2011/0174860 A1 | 7/2011 | Shelton, IV et al. | |
| 2011/0174863 A1 | 7/2011 | Shelton, IV et al. | |
| 2011/0192882 A1 | 8/2011 | Hess et al. | |
| 2011/0226837 A1 | 9/2011 | Baxter, III et al. | |
| 2011/0233258 A1 | 9/2011 | Boudreaux | |
| 2011/0253766 A1 | 10/2011 | Baxter, III et al. | |
| 2011/0288573 A1 | 11/2011 | Yates et al. | |
| 2011/0290851 A1 | 12/2011 | Shelton, IV | |
| 2011/0290853 A1 | 12/2011 | Shelton, IV et al. | |
| 2011/0290854 A1 | 12/2011 | Timm et al. | |
| 2011/0290855 A1 | 12/2011 | Moore et al. | |
| 2011/0290856 A1 | 12/2011 | Shelton, IV et al. | |
| 2011/0290857 A1 | 12/2011 | Shelton, IV et al. | |
| 2011/0295242 A1 | 12/2011 | Spivey et al. | |
| 2011/0295269 A1 | 12/2011 | Swensgard et al. | |
| 2011/0295270 A1 | 12/2011 | Giordano et al. | |
| 2011/0295295 A1 | 12/2011 | Shelton, IV et al. | |

FOREIGN PATENT DOCUMENTS

| | | | |
|---|---|---|---|
| CA | 2514274 A1 | 1/2006 | |
| CN | 1868411 A | 11/2006 | |
| CN | 1915180 A | 2/2007 | |
| DE | 273689 C | 5/1914 | |
| DE | 1775926 A | 1/1972 | |
| DE | 3036217 A1 | 4/1982 | |
| DE | 3210466 A1 | 9/1983 | |
| DE | 9412228 U | 9/1994 | |
| DE | 19509116 A1 | 9/1996 | |
| DE | 19851291 A1 | 1/2000 | |
| DE | 19924311 A1 | 11/2000 | |
| DE | 69328576 T2 | 1/2001 | |
| DE | 10052679 A1 | 5/2001 | |
| DE | 20112837 U1 | 10/2001 | |
| DE | 20121753 U1 | 4/2003 | |
| DE | 10314072 A1 | 10/2004 | |
| DE | 202007003114 U1 | 6/2007 | |
| EP | 0122046 A1 | 10/1984 | |
| EP | 0070230 B1 | 10/1985 | |
| EP | 0387980 B1 | 10/1985 | |
| EP | 0033548 B1 | 5/1986 | |
| EP | 0276104 A2 | 7/1988 | |
| EP | 0248844 B1 | 1/1993 | |
| EP | 0545029 A1 | 6/1993 | |
| EP | 0277959 B1 | 10/1993 | |
| EP | 0233940 B1 | 11/1993 | |
| EP | 0261230 B1 | 11/1993 | |
| EP | 0639349 A2 | 2/1994 | |
| EP | 0324636 B1 | 3/1994 | |
| EP | 0593920 A1 | 4/1994 | |
| EP | 0523174 B1 | 6/1994 | |
| EP | 0600182 A2 | 6/1994 | |
| EP | 0310431 B1 | 11/1994 | |
| EP | 0375302 B1 | 11/1994 | |
| EP | 0376562 B1 | 11/1994 | |
| EP | 0630612 A1 | 12/1994 | |
| EP | 0634144 A1 | 1/1995 | |
| EP | 0646356 A2 | 4/1995 | |
| EP | 0646357 A1 | 4/1995 | |
| EP | 0653189 A2 | 5/1995 | |
| EP | 0669104 A1 | 8/1995 | |
| EP | 0511470 B1 | 10/1995 | |
| EP | 0679367 A2 | 11/1995 | |
| EP | 0392547 B1 | 12/1995 | |
| EP | 0685204 A1 | 12/1995 | |
| EP | 0364216 B1 | 1/1996 | |
| EP | 0699418 A1 | 3/1996 | |
| EP | 0702937 A1 | 3/1996 | |
| EP | 0705571 A1 | 4/1996 | |
| EP | 0711611 A2 | 5/1996 | |
| EP | 0484677 B2 | 6/1996 | |
| EP | 0541987 B1 | 7/1996 | |
| EP | 0667119 B1 | 7/1996 | |
| EP | 0708618 B1 | 3/1997 | |
| EP | 0770355 A1 | 5/1997 | |
| EP | 0503662 B1 | 6/1997 | |
| EP | 0447121 B1 | 7/1997 | |
| EP | 0625077 B1 | 7/1997 | |
| EP | 0633749 B1 | 8/1997 | |
| EP | 0710090 B1 | 8/1997 | |
| EP | 0578425 B1 | 9/1997 | |
| EP | 0625335 B1 | 11/1997 | |
| EP | 0552423 B1 | 1/1998 | |
| EP | 0592244 B1 | 1/1998 | |
| EP | 0648476 B1 | 1/1998 | |
| EP | 0649290 B1 | 3/1998 | |
| EP | 0598618 B1 | 9/1998 | |
| EP | 0676173 B1 | 9/1998 | |
| EP | 0678007 B1 | 9/1998 | |
| EP | 0603472 B1 | 11/1998 | |
| EP | 0605351 B1 | 11/1998 | |
| EP | 0878169 A1 | 11/1998 | |
| EP | 0879742 A1 | 11/1998 | |
| EP | 0695144 B1 | 12/1998 | |
| EP | 0722296 B1 | 12/1998 | |
| EP | 0760230 B1 | 2/1999 | |
| EP | 0623316 B1 | 3/1999 | |
| EP | 0650701 B1 | 3/1999 | |
| EP | 0537572 B1 | 6/1999 | |
| EP | 0923907 A1 | 6/1999 | |
| EP | 0843906 B1 | 3/2000 | |
| EP | 0552050 B1 | 5/2000 | |
| EP | 0833592 B1 | 5/2000 | |
| EP | 0830094 B1 | 9/2000 | |
| EP | 1034747 A1 | 9/2000 | |
| EP | 1034748 A1 | 9/2000 | |
| EP | 0694290 B1 | 11/2000 | |
| EP | 1050278 A1 | 11/2000 | |
| EP | 1053719 A1 | 11/2000 | |
| EP | 1053720 A1 | 11/2000 | |

| | | | | | | |
|---|---|---|---|---|---|---|
| EP | 1055399 | A1 | 11/2000 | EP | 1617768 B1 | 8/2006 |
| EP | 1055400 | A1 | 11/2000 | EP | 1693015 A2 | 8/2006 |
| EP | 1080694 | A1 | 3/2001 | EP | 1400214 B1 | 9/2006 |
| EP | 1090592 | A1 | 4/2001 | EP | 1702567 A2 | 9/2006 |
| EP | 1095627 | A1 | 5/2001 | EP | 1129665 B1 | 11/2006 |
| EP | 1256318 | B1 | 5/2001 | EP | 1400206 B1 | 11/2006 |
| EP | 0806914 | B1 | 9/2001 | EP | 1721568 A1 | 11/2006 |
| EP | 0768840 | B1 | 12/2001 | EP | 1256317 B1 | 12/2006 |
| EP | 0908152 | B1 | 1/2002 | EP | 1728473 A1 | 12/2006 |
| EP | 0872213 | B1 | 5/2002 | EP | 1728475 A2 | 12/2006 |
| EP | 0862386 | B1 | 6/2002 | EP | 1479346 B1 | 1/2007 |
| EP | 0949886 | B1 | 9/2002 | EP | 1484024 B1 | 1/2007 |
| EP | 1238634 | A2 | 9/2002 | EP | 1754445 A2 | 2/2007 |
| EP | 0858295 | B1 | 12/2002 | EP | 1759812 A1 | 3/2007 |
| EP | 0656188 | B1 | 1/2003 | EP | 1767163 A1 | 3/2007 |
| EP | 1284120 | A1 | 2/2003 | EP | 1769756 A1 | 4/2007 |
| EP | 1287788 | A1 | 3/2003 | EP | 1769758 A1 | 4/2007 |
| EP | 0717966 | B1 | 4/2003 | EP | 1581128 B1 | 5/2007 |
| EP | 0869742 | B1 | 5/2003 | EP | 1785097 A2 | 5/2007 |
| EP | 0829235 | B1 | 6/2003 | EP | 1790293 A2 | 5/2007 |
| EP | 0887046 | B1 | 7/2003 | EP | 1800610 A1 | 6/2007 |
| EP | 0852480 | B1 | 8/2003 | EP | 1300117 B1 | 8/2007 |
| EP | 0891154 | B1 | 9/2003 | EP | 1813199 A1 | 8/2007 |
| EP | 0813843 | B1 | 10/2003 | EP | 1813201 A1 | 8/2007 |
| EP | 0873089 | B1 | 10/2003 | EP | 1813203 A2 | 8/2007 |
| EP | 0856326 | B1 | 11/2003 | EP | 1813207 A1 | 8/2007 |
| EP | 1374788 | A1 | 1/2004 | EP | 1813209 A1 | 8/2007 |
| EP | 0741996 | B1 | 2/2004 | EP | 1487359 B1 | 10/2007 |
| EP | 0814712 | B1 | 2/2004 | EP | 1599146 B1 | 10/2007 |
| EP | 1402837 | A1 | 3/2004 | EP | 1839596 A1 | 10/2007 |
| EP | 0705570 | B1 | 4/2004 | EP | 1402821 B1 | 12/2007 |
| EP | 0959784 | B1 | 4/2004 | EP | 1872727 A1 | 1/2008 |
| EP | 1407719 | A2 | 4/2004 | EP | 1897502 A1 | 3/2008 |
| EP | 1086713 | B1 | 5/2004 | EP | 1330201 B1 | 6/2008 |
| EP | 0996378 | B1 | 6/2004 | EP | 1702568 B1 | 7/2008 |
| EP | 1426012 | A1 | 6/2004 | EP | 1943976 A2 | 7/2008 |
| EP | 0833593 | B2 | 7/2004 | EP | 1593337 B1 | 8/2008 |
| EP | 1442694 | A1 | 8/2004 | EP | 1970014 A1 | 9/2008 |
| EP | 0888749 | B1 | 9/2004 | EP | 1980213 A2 | 10/2008 |
| EP | 0959786 | B1 | 9/2004 | EP | 1759645 B1 | 11/2008 |
| EP | 1459695 | A1 | 9/2004 | EP | 1990014 A2 | 11/2008 |
| EP | 1473819 | A1 | 11/2004 | EP | 1693008 B1 | 12/2008 |
| EP | 1477119 | A1 | 11/2004 | EP | 1759640 B1 | 12/2008 |
| EP | 1479345 | A1 | 11/2004 | EP | 2000102 A2 | 12/2008 |
| EP | 1479347 | A1 | 11/2004 | EP | 1736104 B1 | 3/2009 |
| EP | 1479348 | A1 | 11/2004 | EP | 1749486 B1 | 3/2009 |
| EP | 0754437 | B2 | 12/2004 | EP | 1721576 B1 | 4/2009 |
| EP | 1025807 | B1 | 12/2004 | EP | 1733686 B1 | 4/2009 |
| EP | 1001710 | B1 | 1/2005 | EP | 1745748 B1 | 8/2009 |
| EP | 1520521 | A1 | 4/2005 | EP | 2090256 A2 | 8/2009 |
| EP | 1520523 | A1 | 4/2005 | EP | 1813208 B1 | 11/2009 |
| EP | 1520525 | A1 | 4/2005 | EP | 1607050 B1 | 12/2009 |
| EP | 1522264 | A1 | 4/2005 | EP | 1566150 B1 | 4/2010 |
| EP | 1523942 | A2 | 4/2005 | EP | 1813206 B1 | 4/2010 |
| EP | 1550408 | A1 | 7/2005 | EP | 1769754 B1 | 6/2010 |
| EP | 1557129 | A1 | 7/2005 | EP | 1535565 B1 | 10/2010 |
| EP | 1064883 | B1 | 8/2005 | EP | 1702570 B1 | 10/2010 |
| EP | 1067876 | B1 | 8/2005 | EP | 1785098 B1 | 10/2010 |
| EP | 0870473 | B1 | 9/2005 | EP | 1813205 B1 | 6/2011 |
| EP | 1157666 | B1 | 9/2005 | FR | 999646 A | 2/1952 |
| EP | 0880338 | B1 | 10/2005 | FR | 1112936 A | 3/1956 |
| EP | 1158917 | B1 | 11/2005 | FR | 2765794 A | 1/1999 |
| EP | 1344498 | B1 | 11/2005 | GB | 939929 A | 10/1963 |
| EP | 1330989 | B1 | 12/2005 | GB | 1210522 A | 10/1970 |
| EP | 0771176 | B2 | 1/2006 | GB | 1217159 A | 12/1970 |
| EP | 1621138 | A2 | 2/2006 | GB | 1339394 A | 12/1973 |
| EP | 1621139 | A2 | 2/2006 | GB | 2109241 A | 6/1983 |
| EP | 1621141 | A2 | 2/2006 | GB | 2272159 A | 5/1994 |
| EP | 1621145 | A2 | 2/2006 | GB | 2284242 A | 5/1995 |
| EP | 1621151 | A2 | 2/2006 | GB | 2336214 A | 10/1999 |
| EP | 1034746 | B1 | 3/2006 | GB | 2425903 A | 11/2006 |
| EP | 1632191 | A2 | 3/2006 | JP | 6007357 A | 1/1994 |
| EP | 1065981 | B1 | 5/2006 | JP | 7051273 A | 2/1995 |
| EP | 1082944 | B1 | 5/2006 | JP | 8033641 A | 2/1996 |
| EP | 1652481 | A2 | 5/2006 | JP | 8229050 A | 9/1996 |
| EP | 1382303 | B1 | 6/2006 | JP | 2000033071 A | 2/2000 |
| EP | 1253866 | B1 | 7/2006 | JP | 2000171730 A | 6/2000 |
| EP | 1032318 | B1 | 8/2006 | JP | 2000287987 A | 10/2000 |
| EP | 1045672 | B1 | 8/2006 | JP | 2000325303 A | 11/2000 |

| | | | | | | | |
|---|---|---|---|---|---|---|---|
| JP | 2001286477 | A | 10/2001 | WO | WO 97/24073 | A1 | 7/1997 |
| JP | 2002143078 | A | 5/2002 | WO | WO 97/24993 | A1 | 7/1997 |
| JP | 2002369820 | A | 12/2002 | WO | WO 97/30644 | A1 | 8/1997 |
| JP | 2005505322 | T | 2/2005 | WO | WO 97/34533 | A1 | 9/1997 |
| JP | 2005103293 | A | 4/2005 | WO | WO 97/37598 | A1 | 10/1997 |
| JP | 2005131163 | A | 5/2005 | WO | WO 97/39688 | A2 | 10/1997 |
| JP | 2005131164 | A | 5/2005 | WO | WO 98/17180 | A1 | 4/1998 |
| JP | 2005131173 | A | 5/2005 | WO | WO 98/27880 | A1 | 7/1998 |
| JP | 2005131211 | A | 5/2005 | WO | WO 98/30153 | A1 | 7/1998 |
| JP | 2005131212 | A | 5/2005 | WO | WO 98/47436 | A1 | 10/1998 |
| JP | 2005137423 | A | 6/2005 | WO | WO 99/03407 | A1 | 1/1999 |
| JP | 2005152416 | A | 6/2005 | WO | WO 99/03408 | A1 | 1/1999 |
| JP | 2006-281405 | A | 10/2006 | WO | WO 99/03409 | A1 | 1/1999 |
| RU | 2008830 | C1 | 3/1994 | WO | WO 99/12483 | A1 | 3/1999 |
| RU | 2187249 | C2 | 8/2002 | WO | WO 99/12487 | A1 | 3/1999 |
| RU | 2225170 | C2 | 3/2004 | WO | WO 99/12488 | A1 | 3/1999 |
| SU | 189517 | A | 1/1967 | WO | WO 99/15086 | A1 | 4/1999 |
| SU | 328636 | A | 9/1972 | WO | WO 99/15091 | A1 | 4/1999 |
| SU | 886900 | A1 | 12/1981 | WO | WO 99/23933 | A2 | 5/1999 |
| SU | 1009439 | A | 4/1983 | WO | WO 99/23959 | A1 | 5/1999 |
| SU | 1333319 | A2 | 8/1987 | WO | WO 99/25261 | A1 | 5/1999 |
| SU | 1377053 | A1 | 2/1988 | WO | WO 99/29244 | A1 | 6/1999 |
| SU | 1561964 | A1 | 5/1990 | WO | WO 99/34744 | A1 | 7/1999 |
| SU | 1722476 | A1 | 3/1992 | WO | WO 99/45849 | A1 | 9/1999 |
| WO | WO 91/15157 | A1 | 10/1991 | WO | WO 99/48430 | A1 | 9/1999 |
| WO | WO 92/20295 | A1 | 11/1992 | WO | WO 99/51158 | A1 | 10/1999 |
| WO | WO 92/21300 | A1 | 12/1992 | WO | WO 00/24322 | A1 | 5/2000 |
| WO | WO 93/08755 | A1 | 5/1993 | WO | WO 00/24330 | A1 | 5/2000 |
| WO | WO 93/13718 | A1 | 7/1993 | WO | WO 00/41638 | A1 | 7/2000 |
| WO | WO 93/14690 | A1 | 8/1993 | WO | WO 00/48506 | A1 | 8/2000 |
| WO | WO 93/15648 | A1 | 8/1993 | WO | WO 00/53112 | A2 | 9/2000 |
| WO | WO 93/15850 | A1 | 8/1993 | WO | WO 00/54653 | A1 | 9/2000 |
| WO | WO 93/19681 | A1 | 10/1993 | WO | WO 00/57796 | A1 | 10/2000 |
| WO | WO 94/00060 | A1 | 1/1994 | WO | WO 00/64365 | A1 | 11/2000 |
| WO | WO 94/11057 | A1 | 5/1994 | WO | WO 00/72762 | A1 | 12/2000 |
| WO | WO 94/12108 | A1 | 6/1994 | WO | WO 00/72765 | A1 | 12/2000 |
| WO | WO 94/18893 | A1 | 9/1994 | WO | WO 01/03587 | A1 | 1/2001 |
| WO | WO 94/22378 | A1 | 10/1994 | WO | WO 01/05702 | A1 | 1/2001 |
| WO | WO 94/23659 | A1 | 10/1994 | WO | WO 01/10482 | A1 | 2/2001 |
| WO | WO 95/02369 | A1 | 1/1995 | WO | WO 01/35845 | A1 | 5/2001 |
| WO | WO 95/03743 | A1 | 2/1995 | WO | WO 01/54594 | A1 | 8/2001 |
| WO | WO 95/06817 | A1 | 3/1995 | WO | WO 01/58371 | A1 | 8/2001 |
| WO | WO 95/09576 | A1 | 4/1995 | WO | WO 01/62158 | A2 | 8/2001 |
| WO | WO 95/09577 | A1 | 4/1995 | WO | WO 01/62161 | A1 | 8/2001 |
| WO | WO 95/14436 | A1 | 6/1995 | WO | WO 01/62162 | A1 | 8/2001 |
| WO | WO 95/17855 | A1 | 7/1995 | WO | WO 01/62164 | A2 | 8/2001 |
| WO | WO 95/18383 | A1 | 7/1995 | WO | WO 01/62169 | A2 | 8/2001 |
| WO | WO 95/18572 | A1 | 7/1995 | WO | WO 01/78605 | A2 | 10/2001 |
| WO | WO 95/19739 | A1 | 7/1995 | WO | WO 01/91646 | A1 | 12/2001 |
| WO | WO 95/20360 | A1 | 8/1995 | WO | WO 02/07608 | A2 | 1/2002 |
| WO | WO 95/23557 | A1 | 9/1995 | WO | WO 02/07618 | A1 | 1/2002 |
| WO | WO 95/24865 | A1 | 9/1995 | WO | WO 02/17799 | A1 | 3/2002 |
| WO | WO 95/25471 | A3 | 9/1995 | WO | WO 02/19920 | A1 | 3/2002 |
| WO | WO 95/26562 | A1 | 10/1995 | WO | WO 02/19932 | A1 | 3/2002 |
| WO | WO 95/29639 | A1 | 11/1995 | WO | WO 02/30297 | A2 | 4/2002 |
| WO | WO 96/04858 | A1 | 2/1996 | WO | WO 02/32322 | A2 | 4/2002 |
| WO | WO 96/19151 | A1 | 6/1996 | WO | WO 02/36028 | A1 | 5/2002 |
| WO | WO 96/19152 | A1 | 6/1996 | WO | WO 02/43571 | A2 | 6/2002 |
| WO | WO 96/20652 | A1 | 7/1996 | WO | WO 02/058568 | A1 | 8/2002 |
| WO | WO 96/21119 | A1 | 7/1996 | WO | WO 02/060328 | A1 | 8/2002 |
| WO | WO 96/22055 | A1 | 7/1996 | WO | WO 02/067785 | A2 | 9/2002 |
| WO | WO 96/23448 | A1 | 8/1996 | WO | WO 02/098302 | A1 | 12/2002 |
| WO | WO 96/24301 | A1 | 8/1996 | WO | WO 03/000138 | A2 | 1/2003 |
| WO | WO 96/27337 | A1 | 9/1996 | WO | WO 03/001329 | A2 | 1/2003 |
| WO | WO 96/31155 | A1 | 10/1996 | WO | WO 03/013363 | A1 | 2/2003 |
| WO | WO 96/35464 | A1 | 11/1996 | WO | WO 03/015604 | A2 | 2/2003 |
| WO | WO 96/39085 | A1 | 12/1996 | WO | WO 03/020106 | A2 | 3/2003 |
| WO | WO 96/39086 | A1 | 12/1996 | WO | WO 03/020139 | A2 | 3/2003 |
| WO | WO 96/39087 | A1 | 12/1996 | WO | WO 03/024339 | A1 | 3/2003 |
| WO | WO 96/39088 | A1 | 12/1996 | WO | WO 03/079909 | A3 | 3/2003 |
| WO | WO 96/39089 | A1 | 12/1996 | WO | WO 03/030743 | A2 | 4/2003 |
| WO | WO 97/00646 | A1 | 1/1997 | WO | WO 03/037193 | A1 | 5/2003 |
| WO | WO 97/00647 | A1 | 1/1997 | WO | WO 03/047436 | A3 | 6/2003 |
| WO | WO 97/06582 | A1 | 2/1997 | WO | WO 03/055402 | A1 | 7/2003 |
| WO | WO 97/10763 | A1 | 3/1997 | WO | WO 03/057048 | A1 | 7/2003 |
| WO | WO 97/10764 | A1 | 3/1997 | WO | WO 03/057058 | A1 | 7/2003 |
| WO | WO 97/11648 | A2 | 4/1997 | WO | WO 03/063694 | A1 | 8/2003 |
| WO | WO 97/11649 | A1 | 4/1997 | WO | WO 03/077769 | A1 | 9/2003 |
| WO | WO 97/15237 | A1 | 5/1997 | WO | WO 03/079911 | A1 | 10/2003 |

| | | |
|---|---|---|
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A1 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/117735 A1 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/109125 A1 | 9/2008 |
| WO | WO 2010/063795 A1 | 6/2010 |

OTHER PUBLICATIONS

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

\* cited by examiner

SURGICAL STAPLE CARTRIDGES WITH TISSUE TETHERS FOR MANIPULATING DIVIDED TISSUE AND METHODS OF USING SAME

BACKGROUND

1. Technical Field

The present invention relates to surgical instruments and, in various embodiments, to surgical cutting and stapling instruments and staple cartridges therefor that are designed to cut and staple tissue.

2. Background

Surgical staplers have been used to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil that has staple-forming pockets aligned with rows of unformed staples supported in the cartridge.

In use, a clinician is able to close the jaw members of the stapler upon tissue to position the tissue prior to firing. Once the clinician has determined that the jaw members are properly gripping tissue, the clinician can then fire the surgical stapler, thereby severing and stapling the tissue. The simultaneous severing and stapling avoids complications that may arise when performing such actions sequentially with different surgical tools that respectively only sever or staple.

A variety of surgical cutting and stapling instruments are known that may be employed laparoscopically and/or in connection with various "open" surgical procedures. Some surgical stapling and severing instruments are configured to support replaceable cartridges that support the unformed staples therein. Such devices commonly employ a retractable cutting member that remains with the stapling instrument and may be reused with several cartridges. After the staples are fired in one cartridge, the cutting member is retracted and the spent cartridge is removed to enable a new cartridge to be installed if desired. As the cutting member is driven distally through the cartridge, the unformed staples are fired out of their respective pockets in the cartridge into forming contact with the underside of the anvil. Examples of such devices are disclosed in U.S. Pat. No. 7,000,818, entitled "Surgical Stapling Instrument Having Separate Distinct Closing and Firing Systems", issued Feb. 21, 2006, the disclosure of which is herein incorporated by reference in its entirety. Other surgical cutting and stapling instruments employ what is commonly referred to as a "disposable loading unit" or "DLU". Such devices support a staple cartridge and a fresh knife in the form of a "unit" that is configured to be operably attached to the surgical stapling instrument. The units are designed to be discarded after the staples have been fired. Examples of such instruments are disclosed in U.S. Pat. No. 5,865,361 entitled "Surgical Stapling Apparatus", issued Feb. 2, 1999, the entire disclosure of which is herein incorporated by reference.

In some circumstances, the layers of tissue can be relatively thin, can have a high fluid content, and/or can have a non-uniform thickness, which can cause the staples to be improperly formed within the tissue. To ameliorate this problem, a piece of "buttress" material has been utilized to support the tissue as the tissue is being clamped and stapled. Such piece of buttress material is commonly releasably attached to at least one of the first and second jaw members before they are inserted into a surgical site. The piece of buttress material serves to distribute the compressive force applied by the staples over the surface area of the tissue in order to create a more uniform pressure distribution within the tissue. U.S. Patent Publication No. US2009/0206143 A1, entitled "Surgical End Effector Having Buttress Retention Features", published Aug. 20, 2009 discloses various buttresses and buttress retention arrangements and is herein incorporated by reference in its entirety.

In many surgical procedures and, in particular, in many vascular-related surgical procedures, once the tissue is divided by the cutting and stapling instrument, the two segments of tissue fall away from the end effector that supports the staple cartridge. In some procedures involving, for example, the bowel and/or stomach, may not be problematic. However, other tissue types such as vessels have a tendency to rapidly withdraw towards their origin after being severed. For example, in a procedure such as a lung lobectomy, wherein the vessels are generally located within a relatively confined thoracic cavity, once a vessel has pulled away, it can be very difficult to reacquire should the need arise. For example, if the sealing or ligation is flawed and there is bleeding, it is imperative that the vessel be reacquired as quickly as possible to undertake repair of the leaking vessel.

Accordingly, there is a need for surgical staple cartridge arrangements that address many of the challenges discussed above.

The foregoing discussion is intended only to illustrate some of the shortcomings present in the field of the invention at the time, and should not be taken as a disavowal of claim scope.

SUMMARY

In accordance with general aspects of at least one form, there is provided a surgical staple cartridge that has a cartridge body that operably supports a plurality of surgical staples therein. A base material is temporarily supported on a portion of the cartridge body and is configured to be stapled to tissue when the staples supported in the cartridge body are stapled into the tissue. The base material is configured to remain attached to the tissue when the cartridge body is withdrawn therefrom. At least one elongated tether is non-removably coupled to the base material.

In accordance with other general aspects of at least one form, there is provided a surgical end effector for use with a surgical instrument. In various embodiments, the surgical end effector comprises an elongated channel that is operably couplable to the surgical instrument. A staple cartridge that has a cartridge body is operably supported in the elongated channel. The cartridge body has a deck surface that is substantially split into a first deck portion and a second deck portion by a longitudinal slot that extends therebetween. The cartridge body operably supports a first plurality of unformed staples therein that correspond to the first deck portion. A second plurality of unformed staples correspond to the second deck portion. A tissue cutting member is operably supported in the cartridge body for axial advancement in the longitudinal slot upon application of a cutting actuation motion thereto by the surgical instrument. An anvil is supported for movable travel toward and away from the deck surface in response to opening and closing motions applied thereto by the surgical instrument. A first base material is removably supported on the first deck portion and at least one first tether is non-removably attached thereto. A second base material is removably supported on the second deck portion and at least one second tether is non-removably attached thereto.

In accordance with still other general aspects of at least one form, there is provided a method for manipulating divided tissue. In various forms, the method comprises dividing a piece of tissue into two separate tissue segments wherein each tissue segment has a severed end. The method further comprises stapling the severed ends of the first and second tissue segments and affixing at least one tether to at least one of the severed ends of the first and second tissue segments during the stapling action. The method further comprises manipulating the severed end having the at least one tether affixed thereto by applying a manipulation motion to the tether.

BRIEF DESCRIPTION OF DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

DETAILED DESCRIPTION

Figure 1:
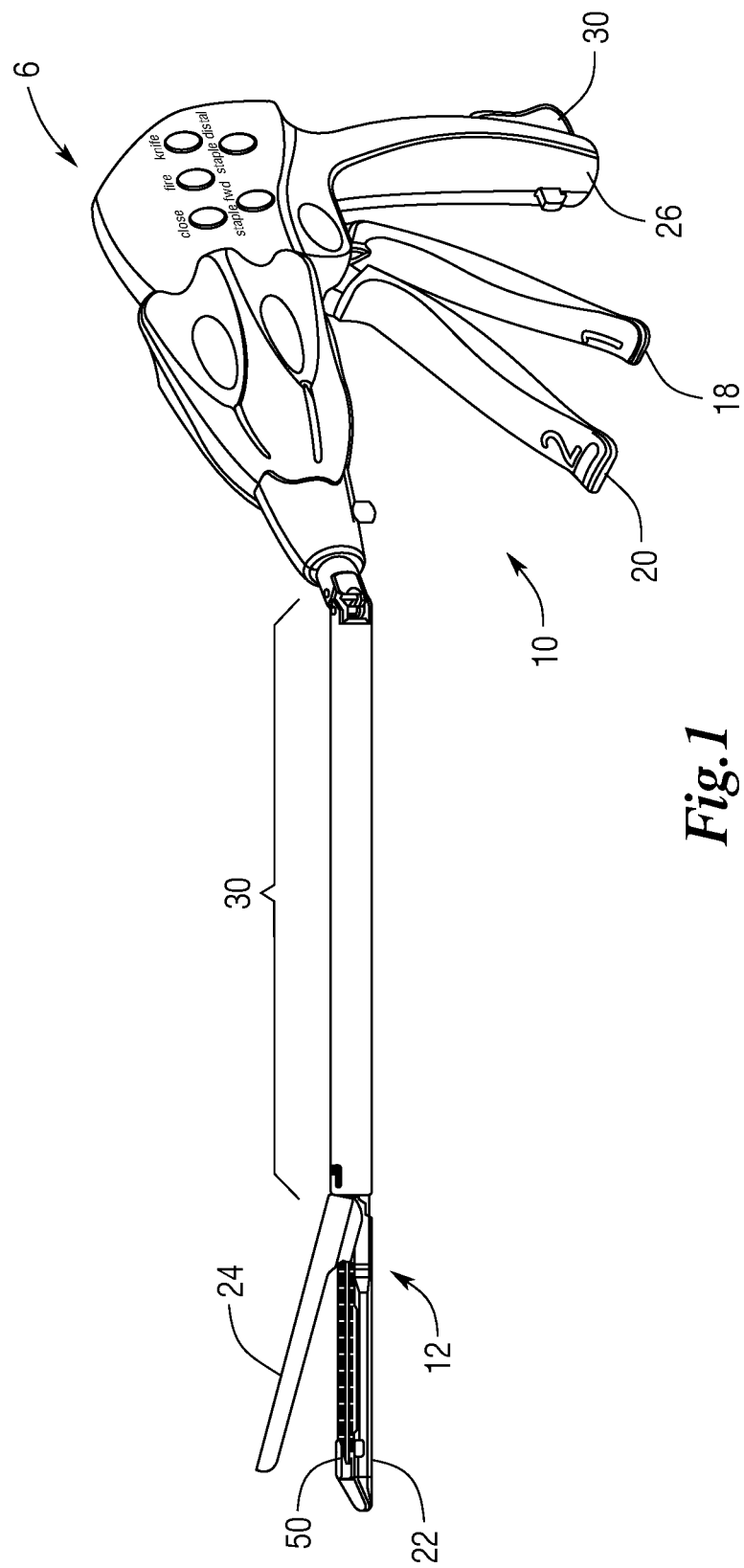
FIG. 1 is a side view of one form of a surgical cutting and stapling instrument with which various cartridges and end effector embodiments of the present invention may be used.

The Applicant of the present application also owns U.S. patent application entitled "Surgical Fastener Instruments", U.S. patent application Ser. No. 13/048,559, U.S. Patent Application Publication No. US-2012-0234899-A1, which was filed on even date herewith and which is herein incorporated by reference in its entirety.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with "open" surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device such as a trocar that has a working channel through which the end effector and elongated shaft of a surgical instrument can be advanced.

Turning to the Drawings wherein like numerals denote like components throughout the several views, FIG. 1 depict one embodiment of a surgical stapling and severing instrument 10 that is capable of practicing various unique benefits of the present invention. Various forms of the surgical instrument 10 are disclosed in U.S. Pat. No. 7,753,904 entitled "Endoscopic Surgical Instrument With a Handle That Can Articulate With Respect to the Shaft", the entire disclosure of which is herein incorporated by reference. As such, the details concerning the construction and operation of that device not needed to understand the various embodiments and forms of the present invention will not be specifically repeated herein. The surgical instrument depicted in FIG. 1 is a motor driven or "powered instrument". As the present Detailed Description proceeds, the skilled artisan will appreciate that the unique and novel aspects of the present invention may also be effectively employed in connection with surgical stapling and severing instruments that employ mechanical (unpowered) systems for firing the staples and cutting tissue without departing from the spirit and scope of the present invention.

As can be seen in FIG. 1, one form of a surgical instrument 10 comprises a handle 6 that has an elongated tube assembly 30 that is operably attached thereto that is configured to transmit actuation motions to an end effector 12 that is attached to a distal end portion of the elongated tube assembly 30. The end effector 12 includes a channel 22 that is coupled to support various forms of staple cartridges of the present invention as will be discussed in greater detail below. An anvil 24 is movably supported relative to the channel 22 in response to opening and closing motions applied thereto by various portions of the elongated tube assembly 30.

Figure 2:
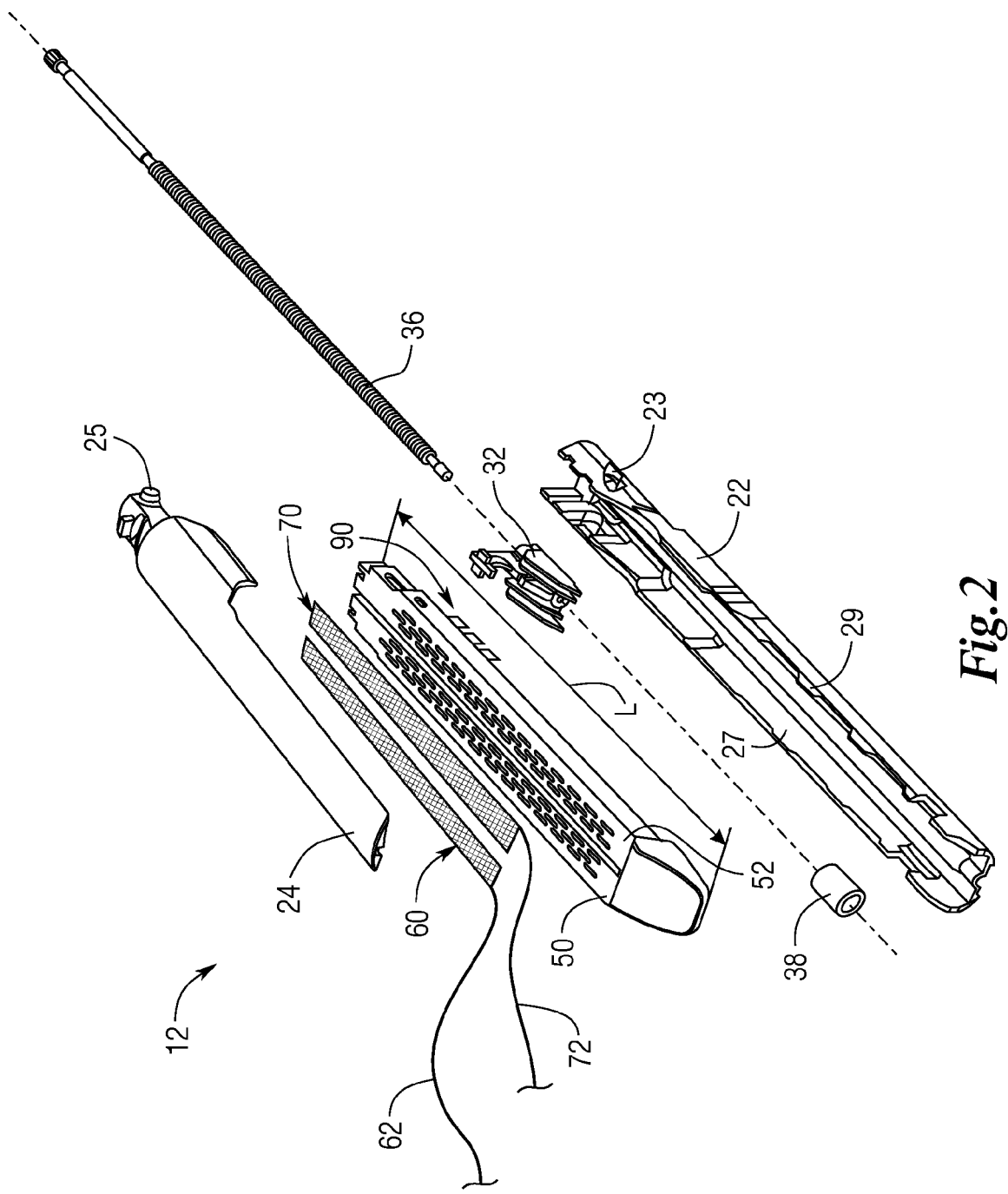
FIG. 2 is an exploded view of an end effector embodiment of the present invention.

The handle 6 includes a pistol grip 26 toward which a closure trigger 18 may be pivotally drawn by the clinician to cause clamping or closing of the anvil 24 toward the staple channel 22 of the end effector 12. A firing trigger 20 is farther outboard of the closure trigger 18. As shown in FIG. 2, the end effector 12 may include, in addition to the previously mentioned channel 22 and anvil 24, a knife and sled driving member 32, a staple cartridge 50 that supports a plurality of unformed staples 90 therein, a helical screw shaft 36 and a bearing 38 that is attached to the channel structure 22. The anvil 24 may be pivotably connected to the channel 22 at a proximate pivot point. In one embodiment, for example, the anvil 24 includes laterally projecting pivot pins 25 at its proximal end that pivotally engage pivot apertures 23 formed near the proximal end of the channel 22. When the closure trigger 18 is actuated, that is, drawn in by a user of the instrument 10, the trunnions 25 of the anvil 24 may pivot within the pivot apertures 23 in the channel 22 about the pivot point into the clamped or closed position. If clamping of the end effector 12 is satisfactory, the operator may actuate the firing trigger 20, which activates a motor/transmission (not shown) in the handle 6 that applies rotary motion to the helical screw shaft 36 to cause the knife/sled driving member 32 to travel along the channel 22, thereby cutting tissue clamped within the end effector 12 and driving the unformed staples 90 into forming contact with the underside of the anvil 24. As used herein, the term "fire" with respect to the staples refers to the actions involved with driving the unformed staples 90 out of their respective staple pockets within the staple cartridge and into forming contact with a corresponding portion of the anvil. As the present Detailed Description proceeds, the reader will appreciate, however, that the unique and novel aspects of the present invention may be advantageously employed in connection with a variety of other surgical staplers and surgical stapler instruments including those surgical stapling units configured for use with so-called disposable loading units such, for example, those devices disclosed in U.S. Patent Application Publication No. 2006/0011699 A1, entitled "Surgical Stapler With Universal Articulation and Tissue Pre-Clamp", the disclosure of which is herein incorporated by reference in its entirety. Accordingly, the scope of protection afforded to the various embodiments of the present invention should not be limited to use with one particular type of surgical stapling instrument.

After the knife/sled driving member 32 has been driven to the distal end of the staple cartridge 50, the clinician releases the firing trigger 20 to enable the firing trigger 20 to return to an open position, which will result in the application of a retraction motion to the knife/sled driving member 32 to cause it to move proximally to a starting position. Once the knife/sled driving member 32 has been moved to a starting position out of the staple cartridge 50, the clinician may unlock the closure trigger 18 by means of a release button 30 on the handle to permit the closure trigger 18 to move to the open position and thereby cause the anvil 24 to pivot open and release the divided and stapled tissue.

Figure 3:
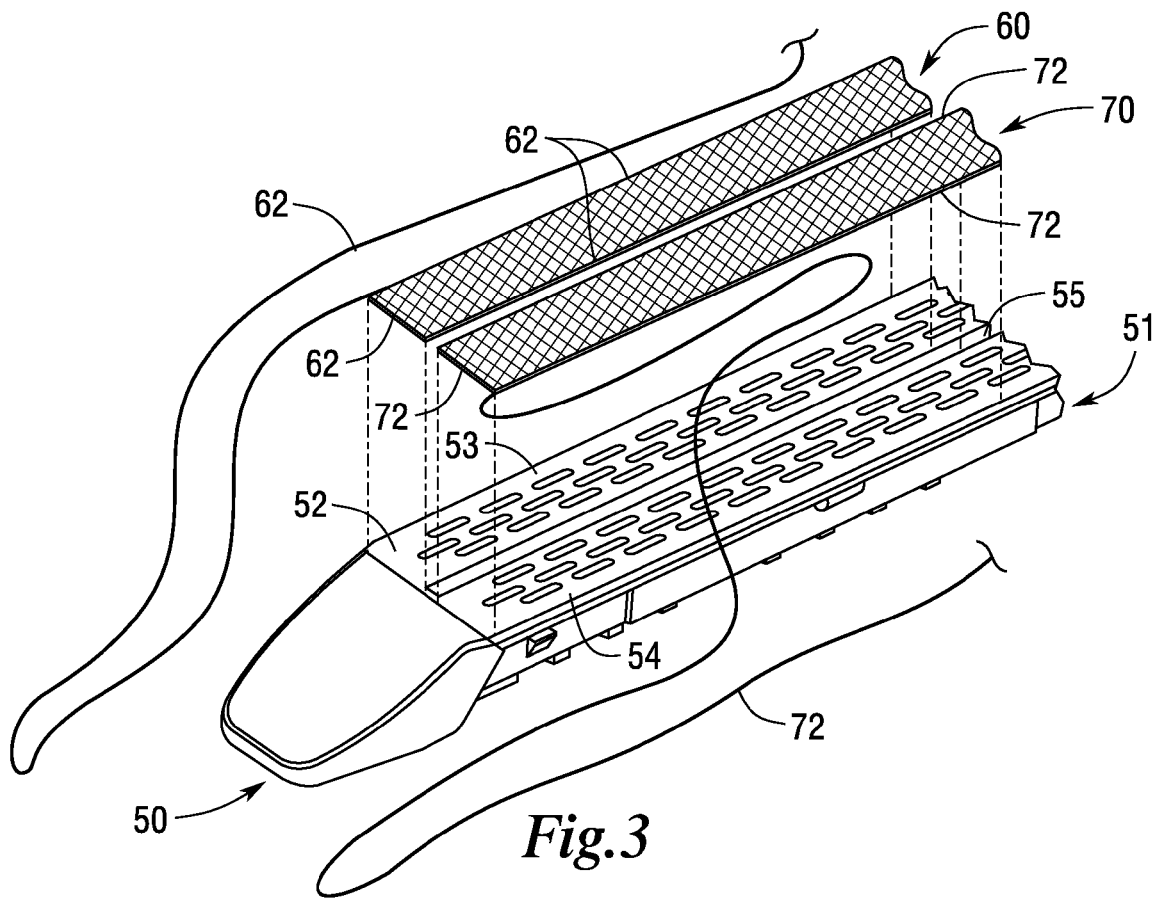
FIG. 3 is an exploded assembly view of a portion of a staple cartridge embodiment of the present invention.
Figure 4:
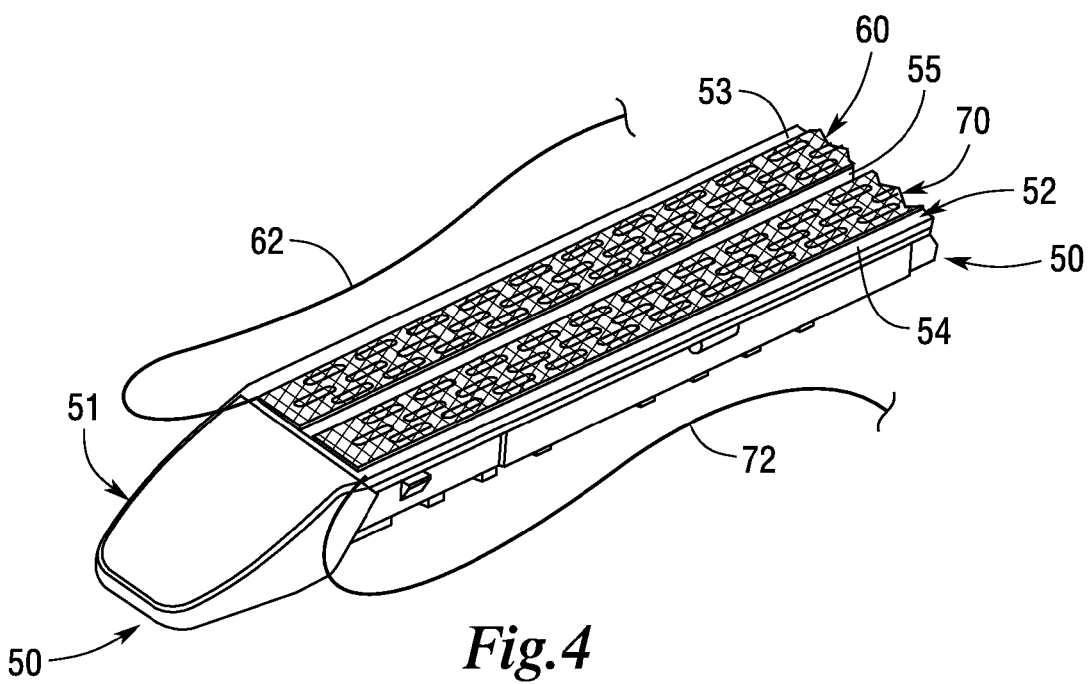
FIG. 4 is a perspective view of a portion of the staple cartridge of FIG. 3.

In the embodiments depicted in FIGS. 3 and 4, the staple cartridge 50 includes a cartridge body 51 that supports a plurality of unformed staples 90 therein. The cartridge body 51 has a centrally disposed slot 55 therein that divides the cartridge deck into a first deck portion 53 and a second deck portion 54. The slot 55 accommodates the knife/sled driving member 32 as it is driven longitudinally within the cartridge body 51. Various embodiments of the present invention include a first base material 60 that is temporarily or removably supported on or attached to the first deck portion 53. Similarly a second material 70 is temporarily or removably supported on or attached to the second deck portion 54. For example, the first and second base materials 60 and 70 may be removably attached to the respective first and second deck portions 53, 54 by adhesives (both natural and man-made), mechanically by deforming portions of the deck or by using biocompatible and/or absorbable fasteners. In various embodiments, the base materials 60 and 70 may be fabricated from a bioabsorbable mesh material. For example, the base materials 60 and 70 may be fabricated from Vicryl (or other absorbable) suture or a coallagen-based material. In other embodiments, the base materials 60 and 70 may be comprise a "buttress" material fabricated from, for example, bovine pericardium, GorTex® material, etc.

Figure 2A:
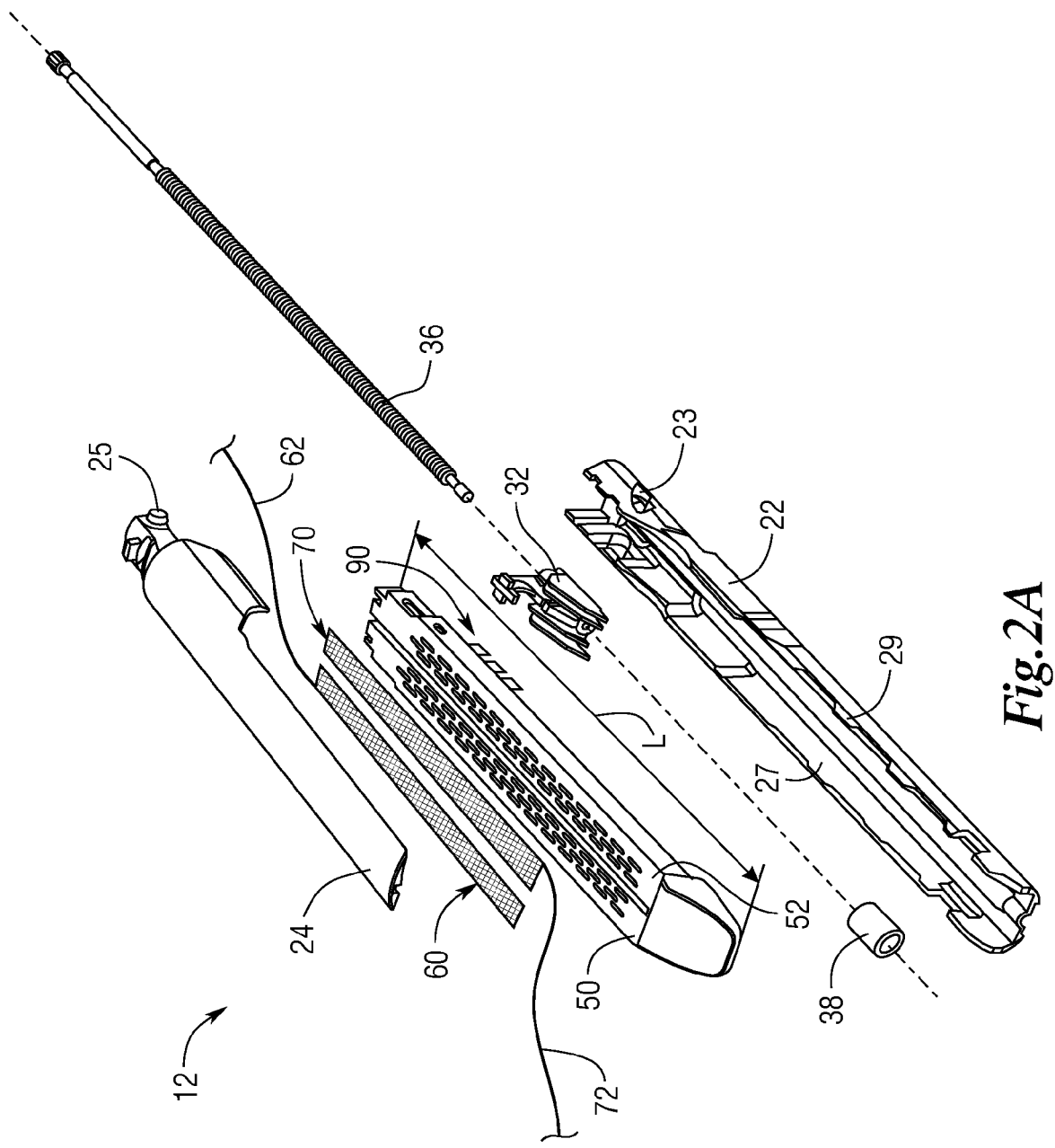
FIG. 2A is an exploded view of another end effector embodiment of the present invention.
Figure 2B:
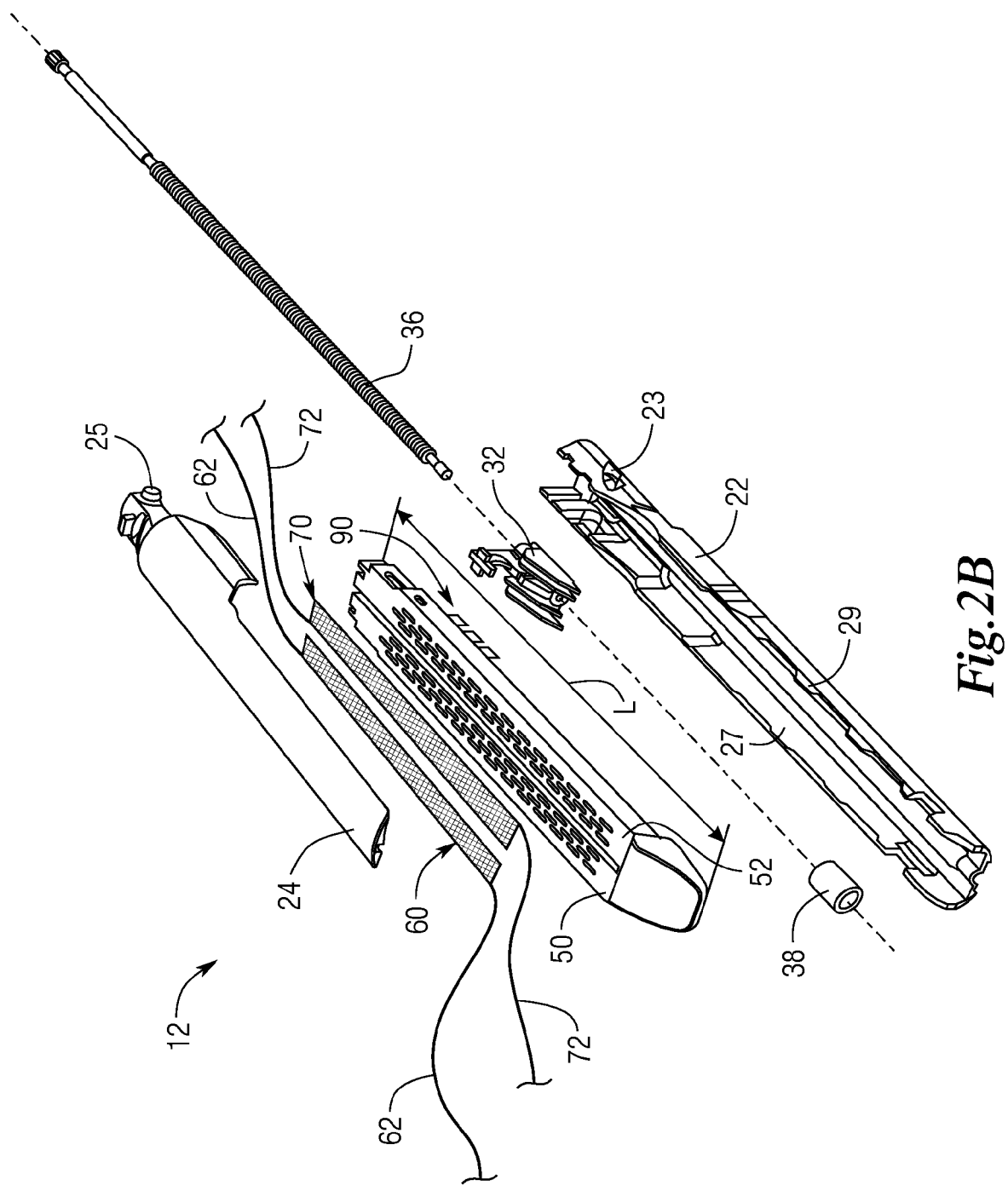
FIG. 2B is an exploded view of another end effector embodiment of the present invention.

As can be seen in FIGS. 3 and 4, for example, various embodiments of the base materials 60 and 70 each have at least one elongated tether attached thereto. In particular, a first elongated tether 62 may extend completely around the first base material 60 and be attached thereto by, for example, adhesives (both natural and man-made), mechanically by deforming portions of the deck, or by using biocompatible and/or absorbably fasteners. In other embodiments, the first elongated tether 62 is attached to a single portion of the first base material (e.g., a corner, side, end, top or bottom surface) such that it extends therefrom. Likewise a second elongated tether 72 is attached to the second base material 70 by the same or similar materials and/or methods. In the embodiment depicted in FIGS. 3 and 4, the first and second elongated tethers 62, 72, respectively, may be provided in various lengths. In one embodiment, for example, the first and second tethers 62, 72 may each have a length that is approximately at least twice the length "L" of the cartridge 50. See FIG. 2. However, the first and second tethers 62, 72 may each have shorter lengths or longer lengths as will be discussed in further detail below. In still other embodiments, one of the elongated tethers 62 or 72 is shorter than the other elongated tether 62 or 72. Although FIG. 2, illustrates attachment of tethers 62 and 72 to the distal ends of the first and second base materials 60, 70, respectively, in other embodiments, the tethers 62, 72 may be attached to the proximal ends of the first and second base materials 60, 70, respectively or in other embodiments, one tether 62 or 72 may be attached to the distal end of its corresponding base material 60, 70 and the other tether 62 or 72 may be attached to the proximal end of its corresponding base material. See FIG. 2A, for example. In still other embodiments, tethers 62, 72 may be attached to both ends of their corresponding base material 60, 70 as shown in FIG. 2B. In yet other embodiments, a tether 62, 72 may be attached to each corner of its respective base material 60, 70.

Figure 5:
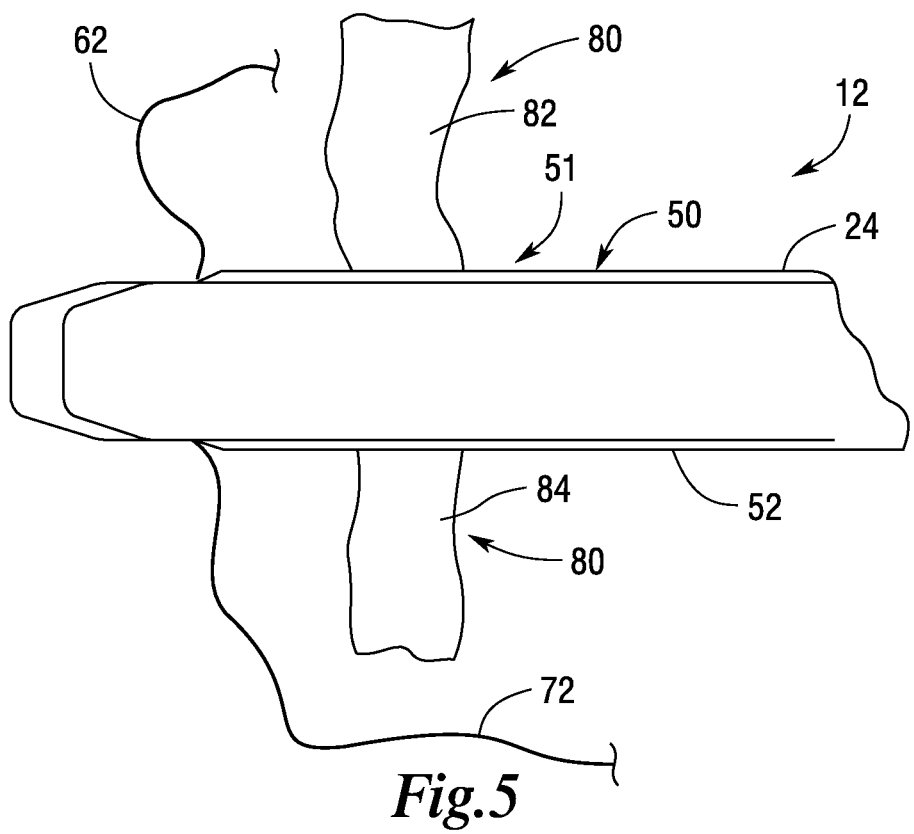
FIG. 5 is a partial plan view of an end effector embodiment clamping a vessel between the anvil and staple cartridge thereof.
Figure 6:
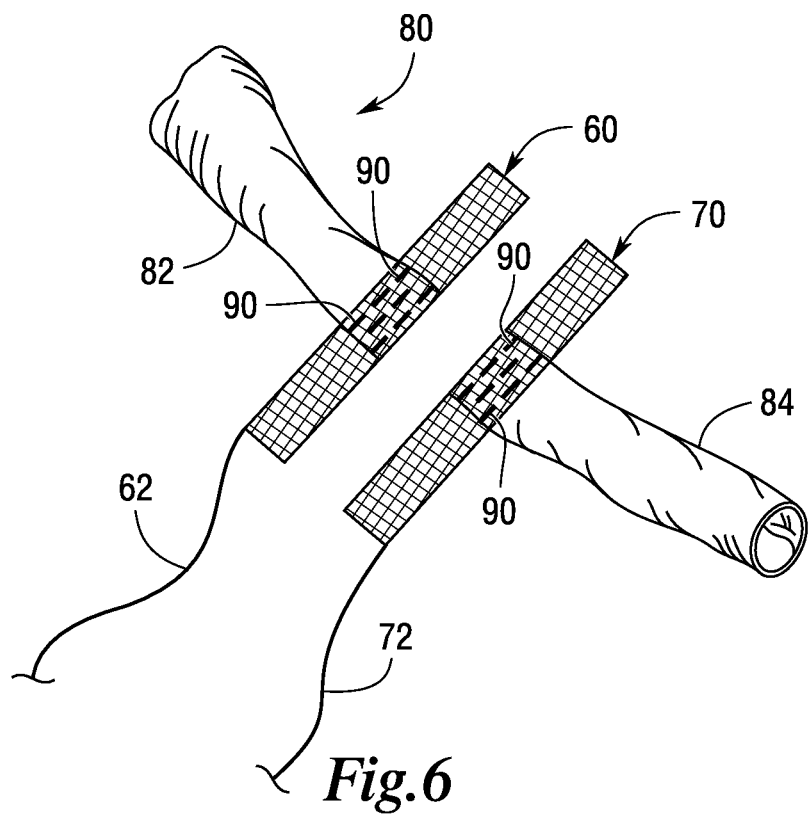
FIG. 6 is a perspective view of the divided and stapled vessel depicted in FIG. 5.

FIGS. 5 and 6 illustrate one use of the staple cartridge 50 for cutting and stapling a vessel 80. As can be seen in FIG. 5, the end effector 12 is positioned relative to the vessel 80 such that the portion of vessel 80 to be cut and stapled is received between the anvil 24 and the deck 52 of the staple cartridge 50. The anvil 24 is then closed (by pulling the closure trigger 18 and locking it in position). The firing trigger 20 may then be depressed to fire the staples 90 and cut the vessel into two vessel ends 82, 84. After firing, the first base material 60 is caught between the crowns of the staples 90 and the first vessel end 82. Likewise, the second base material 70 is caught between the crowns of the staples 90 and the second vessel end 84. See FIG. 6. After the cutting and stapling actions have been completed and the anvil 24 is moved to an open position to release the divided vessel ends 82, 84 from the end effector 12, the end effector 12 may be withdrawn from the site. In this embodiment, the tethers 62, 72 were not previously attached to the cartridge body 51 and remain hanging from their respective first and second base materials 60, 70. Thus, should the clinician need to retrieve or identify the divided vessel ends 82, 84, he or she can find the corresponding tethers 62, 72 and either use a separate instrument (e.g., a grasper, forceps, etc.) to bring the vessel end closer. Such arrangement represents a vast improvement over prior cutting and stapling devices and methods particularly when employed to cut tissue that may need to be further manipulated after stapling.

Figure 7:
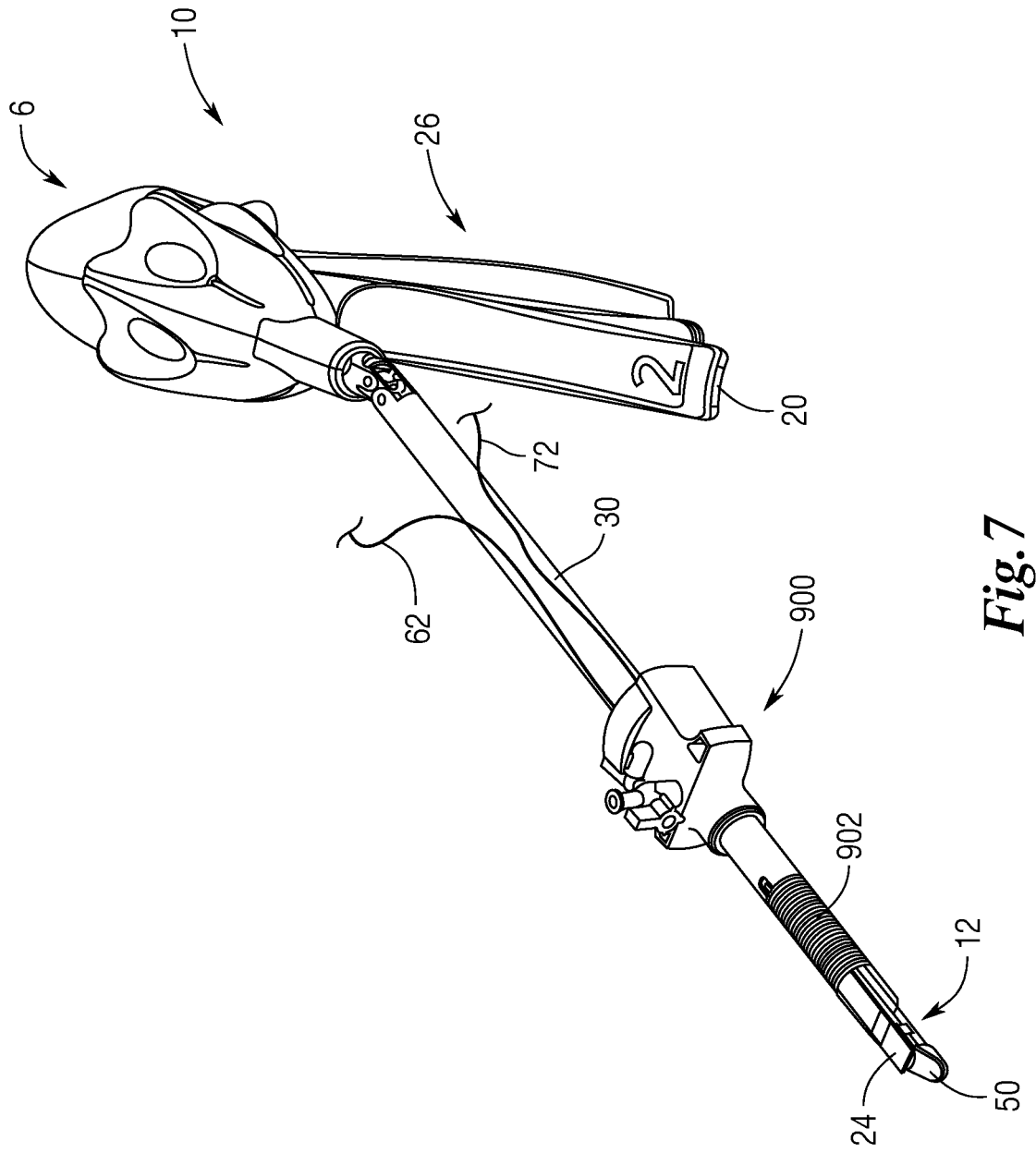
FIG. 7 is a perspective view of a surgical cutting and stapling instrument that has a surgical staple cartridge embodiment of the present invention supported therein that has been inserted into a trocar cannula.

As shown in FIG. 7, the end effector 12 and the elongated shaft assembly 30 may be sized to be inserted through a trocar assembly 900 that has been inserted into the patient. Such trocar assemblies are known in the art and therefore, its construction and operation are not discussed in detail herein. For example, U.S. Pat. No. 6,017,356 to Frederick et al., entitled "Method For Using a Trocar For Penetration and Skin Incision", the disclosure of which is herein incorporated by reference in its entirety discloses various trocar assemblies. The reader will of course appreciate, however, that the various embodiments of the present invention may be effectively employed with a variety of different trocar, cannula, etc. arrangements without departing from the spirit and scope of the present invention. Therefore, the various embodiments of the present invention and their equivalent structures should not in any way be limited to use with the specific type of trocar described herein by way of example.

When used in connection with a trocar, cannula, etc. that provides an access passage into the surgical site within the patient, the first and second tethers 62, 72, respectively may be provided with a length that enables the tethers 62, 72 to extend outside of the trocar 900 to provide easy access thereto. In such arrangements, for example, if one staple line is attached to a portion of tissue destined for excision, the tether could be used to pull that tissue toward the trocar cannula 902 for exit therethrough. See FIG. 7. Such unique and novel arrangement may also be employed when the trocar has been removed, but the tether(s) extend out of the opening in the body cavity. Thus, the tether(s) may be used to manipulate the stapled tissue from outside of the body cavity even after the trocar has been removed.

Figure 8:
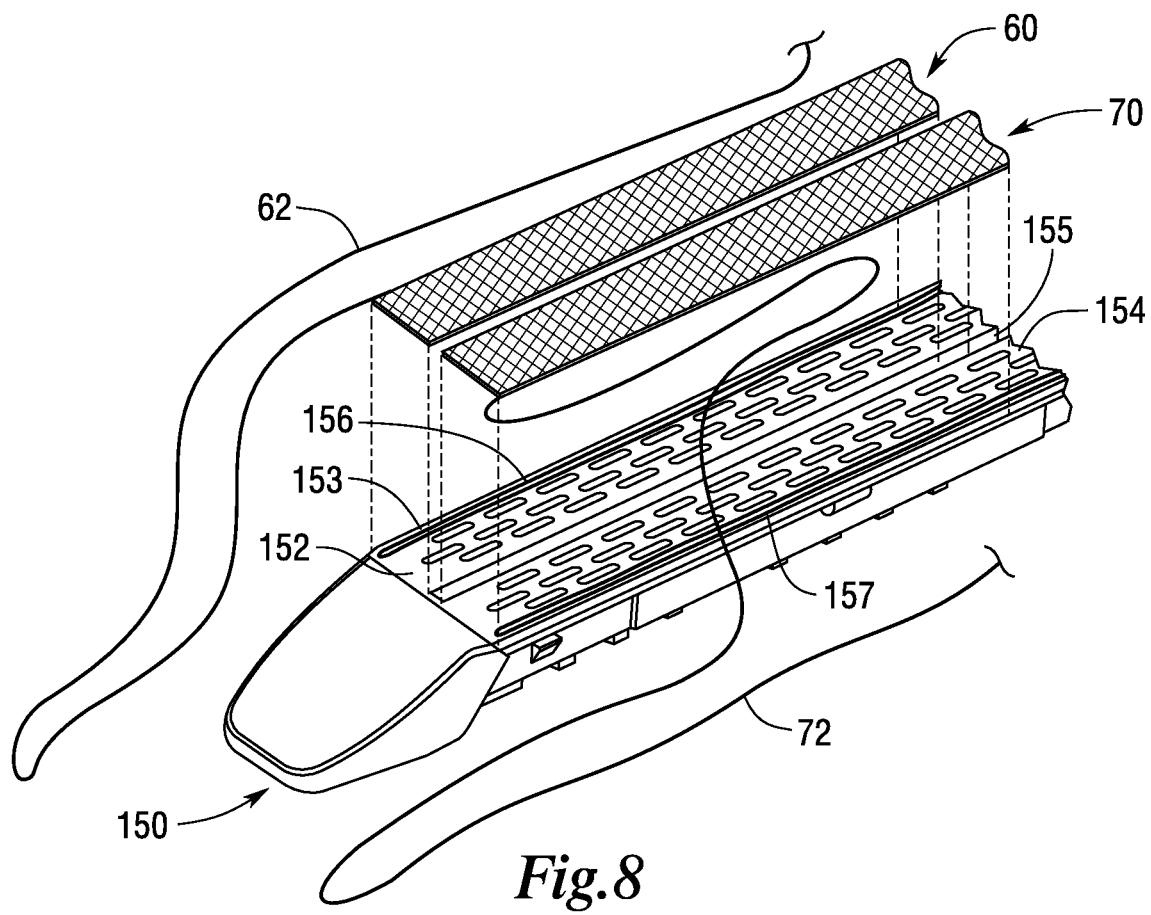
FIG. 8 is an exploded assembly view of a portion of another staple cartridge embodiment of the present invention.
Figure 9:
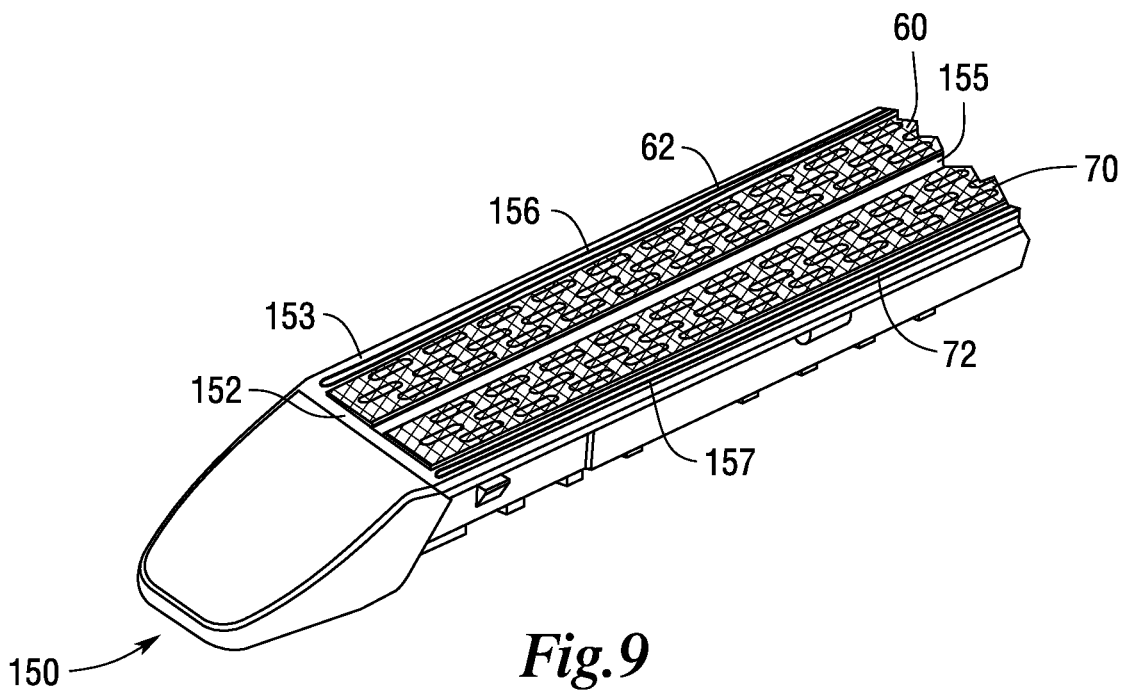
FIG. 9 is a perspective view of a portion of the staple cartridge of FIG. 8.

FIGS. 8 and 9 illustrate another cartridge embodiment 150 that is substantially identical to cartridge 50 described above, except for the differences noted below. In this embodiment for example, the cartridge 150 has a cartridge deck 152 that is divided into a first deck portion 153 and a second deck portion 154 by a slot 155. The first base material 60 is temporarily attached to or removably supported on the first deck portion 153 and the second base material 70 is temporarily attached to or removably attached to or supported on the second deck portion 154 in the various manners described above. In this embodiment, however, a first groove or pocket 156 that is adapted to temporarily receive at least a portion of the first tether 62 therein is provided in the first deck portion 153. Similarly, a second groove or pocket 157 is formed in the second deck portion 154 for temporarily receiving at least a portion of the second tether 72 therein. See FIG. 9. The first groove or pocket 156 may be sized relative to the first tether 62 such that it may be pressed therein to retain it within the groove 156 while the end effector 12 is introduced to the surgical site and then is drawn out of the first groove 156 after the first base material 60 has been affixed to the tissue and the end effector 12 is withdrawn from the surgical site. Likewise, the second groove 157 may be sized relative to the second tether 72 such that it may be pressed therein to retain it within the groove 157 while the end effector 12 is introduced to the surgical site and then is drawn out of the second groove 157 after the second base material 70 has been affixed to the tissue and the end effector 12 is withdrawn from the surgical site. In other embodiments, the first tether 62 may be temporarily retained within the first groove 156 by biocompatible adhesive, gel, etc. and the second tether 72 may be temporarily retained within the second groove 157 by biocompatible adhesive, gel, etc.

Figure 10:
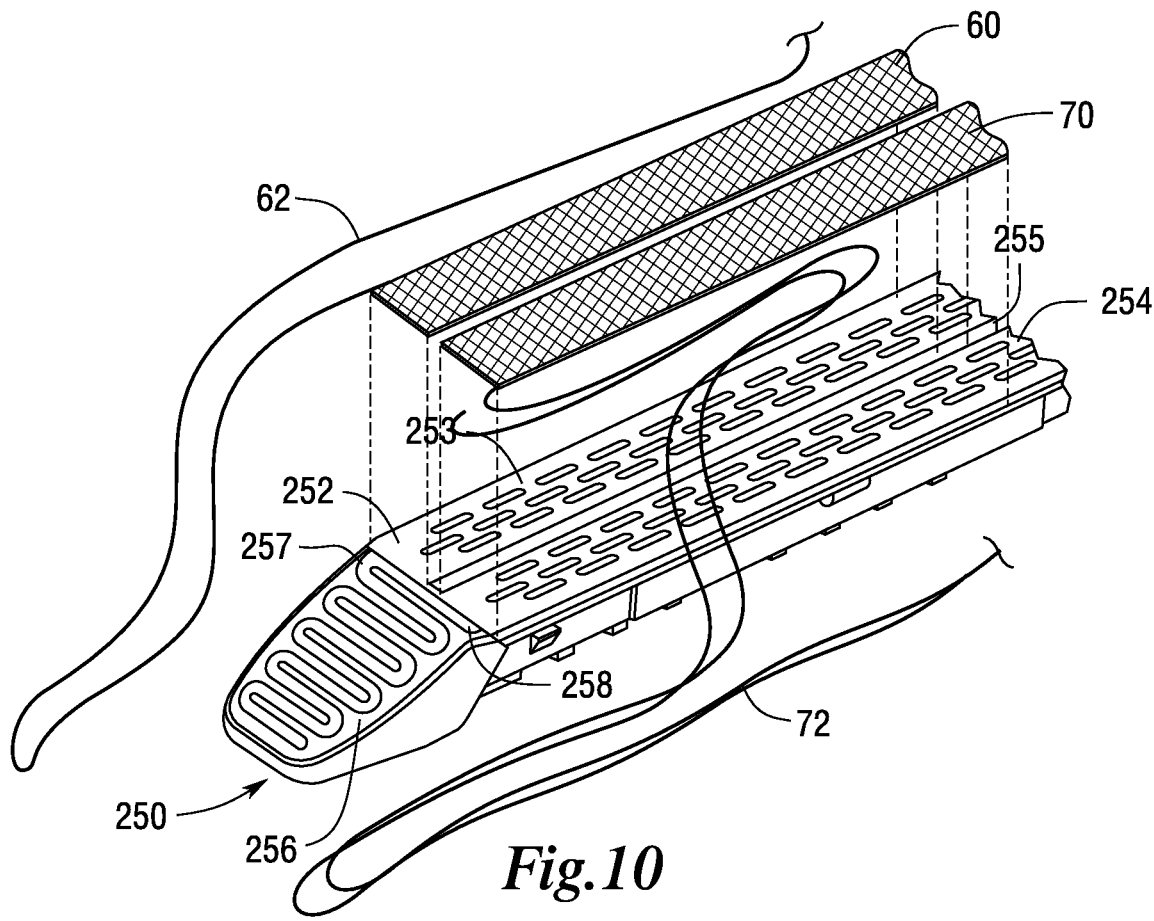
FIG. 10 is an exploded assembly view of a portion of another staple cartridge embodiment of the present invention.
Figure 11:
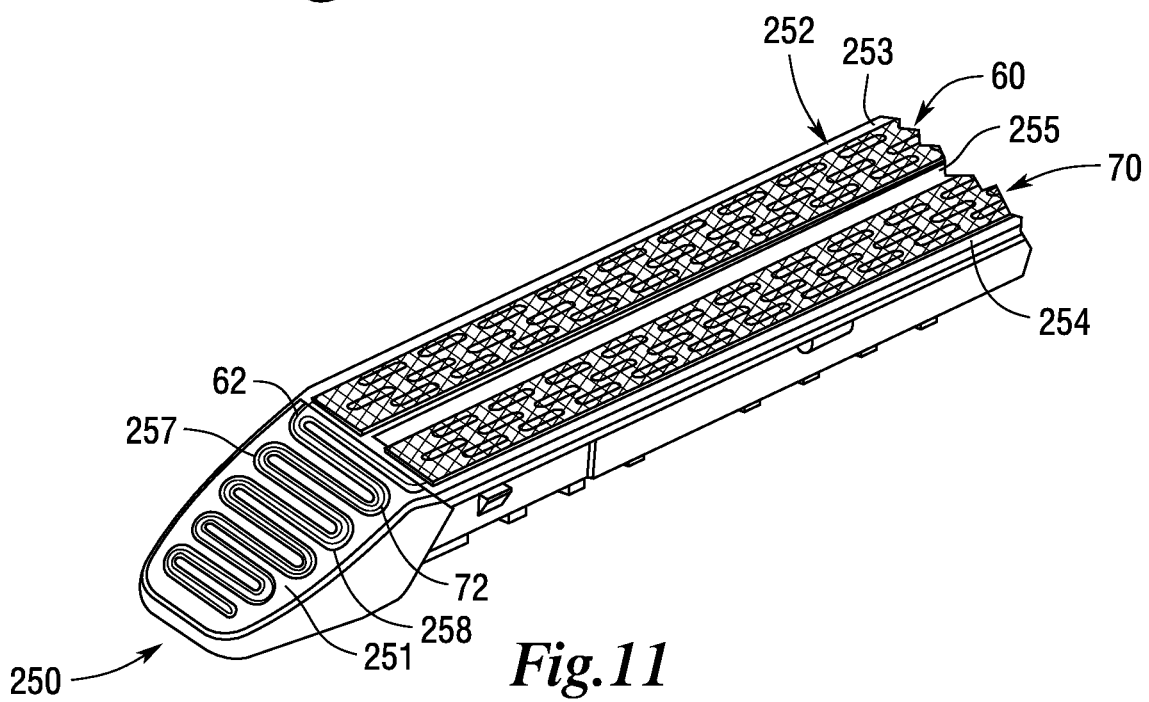
FIG. 11 is a perspective view of a portion of the staple cartridge of FIG. 10.

FIGS. 10 and 11 illustrate another cartridge embodiment 250 that is substantially identical to cartridge 50 described above, except for the differences noted below. In this embodiment for example, the cartridge 250 has a cartridge deck 252 that is divided into a first deck portion 253 and a second deck portion 254 by an elongated slot 255. The first base material 60 is temporarily attached to or removably attached to or supported on the first deck portion 253. Likewise, the second base material 70 is temporarily attached to or removably attached to or supported on the second deck portion 254 in the various manners described above. In this embodiment, however, a first groove, pocket, zone or region 257 that is adapted to temporarily receive at least a portion of the first tether 62 therein is provided in the cartridge nose portion 256. Similarly, a second groove, pocket, zone or region 258 or pocket is formed in the cartridge nose portion 256 for temporarily receiving at least a portion of the second tether 72 therein. See FIG. 11. The first groove or pocket 257 may be sized relative to the first tether 62 such that it may be pressed therein to retain it within the groove 257 while the end effector 12 is introduced to the surgical site and then is drawn out of the first groove 257 after the first base material 60 has been affixed to the tissue and the end effector 12 is withdrawn from the surgical site. Likewise, the second groove 258 may be sized relative to the second tether 72 such that it may be pressed therein to retain it within the groove 258 while the end effector 12 is introduced to the surgical site and then is drawn out of the second groove 258 after the second base material 70 has been affixed to the tissue and the end effector is withdrawn from the surgical site. In other embodiments, the first tether 62 may be temporarily retained within the first groove 257 by adhesive or friction and the second tether 72 may be temporarily retained within the second groove 258 by adhesive or friction.

Figure 12:
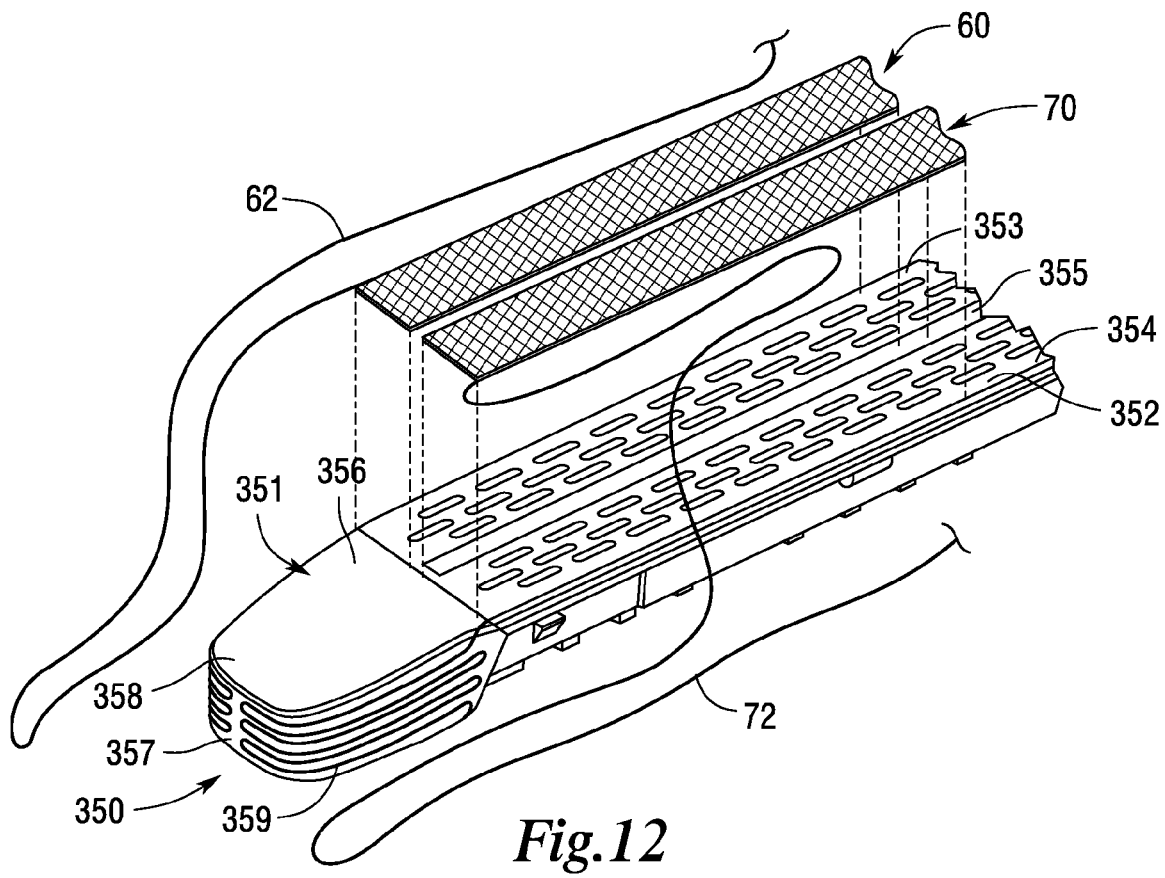
FIG. 12 is an exploded assembly view of a portion of another staple cartridge embodiment of the present invention.
Figure 13:
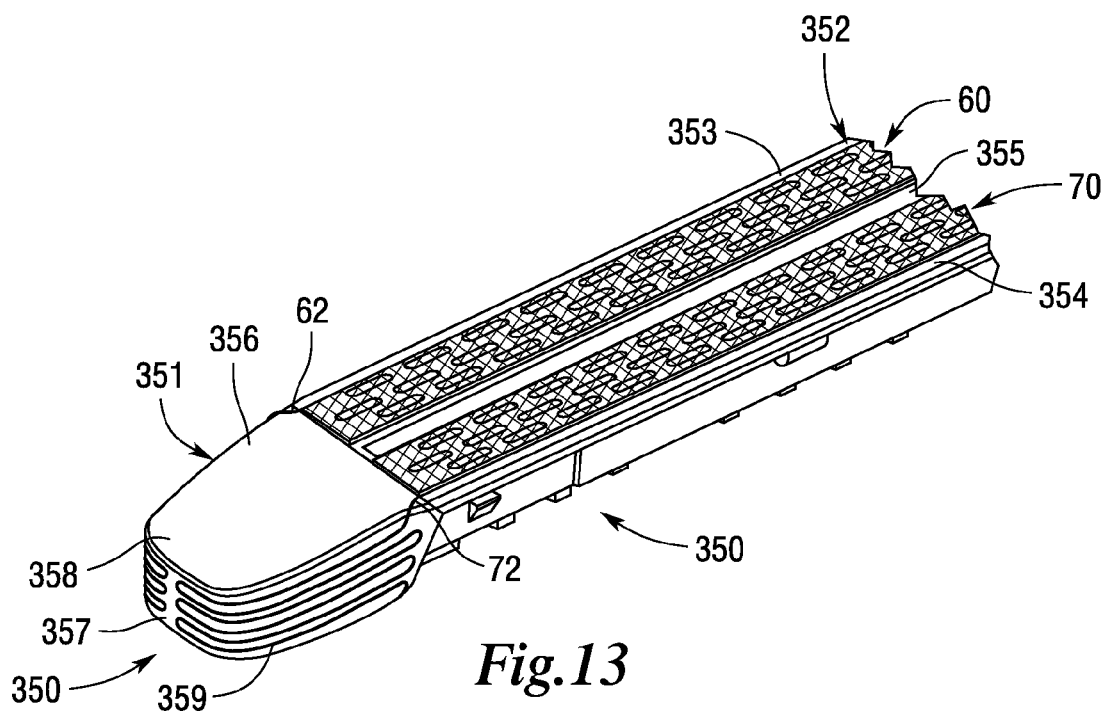
FIG. 13 is a perspective view of a portion of the staple cartridge of FIG. 12.

FIGS. 12 and 13 illustrate another cartridge embodiment 350 that is substantially identical to cartridge 50 described above, except for the differences noted below. In this embodiment for example, the cartridge 350 has a cartridge body 351 that has a cartridge deck 352 that is divided into a first deck portion 353 and a second deck portion 354 by an elongated slot 355. The first base material 60 is temporarily attached to or removably attached to or supported on the first deck portion 353. Likewise, the second base material 70 is temporarily attached to or removably attached to or supported on the second deck portion 354 in the various manners described above. In this embodiment, however, a first groove, pocket, zone or region 358 that is adapted to temporarily receive at least a portion of the first tether 62 therein is provided in the side 357 of the cartridge nose portion 356. Similarly, a second groove, pocket, zone or region 359 is formed in the side 357 of the cartridge nose portion 356 for temporarily receiving at least a portion of the second tether 72 therein. See FIG. 13. The first groove or pocket 358 may be sized relative to the first tether 62 such that it may be pressed therein to retain it within the groove 358 while the end effector 12 is introduced to the surgical site and then is drawn out of the first groove 358 after the first base material 60 has been affixed to the tissue and the end effector 12 is withdrawn from the surgical site. Likewise, the second groove 359 may be sized relative to the second tether 72 such that it may be pressed therein to retain it within the second groove 359 while the end effector 12 is introduced to the surgical site and then is drawn out of the second groove 359 after the second base material 70 has been affixed to the tissue and the end effector 12 is withdrawn from the surgical site. In other embodiments, the first tether 62 may be temporarily retained within the first groove 358 by adhesive or friction and the second tether 72 may be temporarily retained within the second groove 359 by adhesive or friction.

Figure 14:
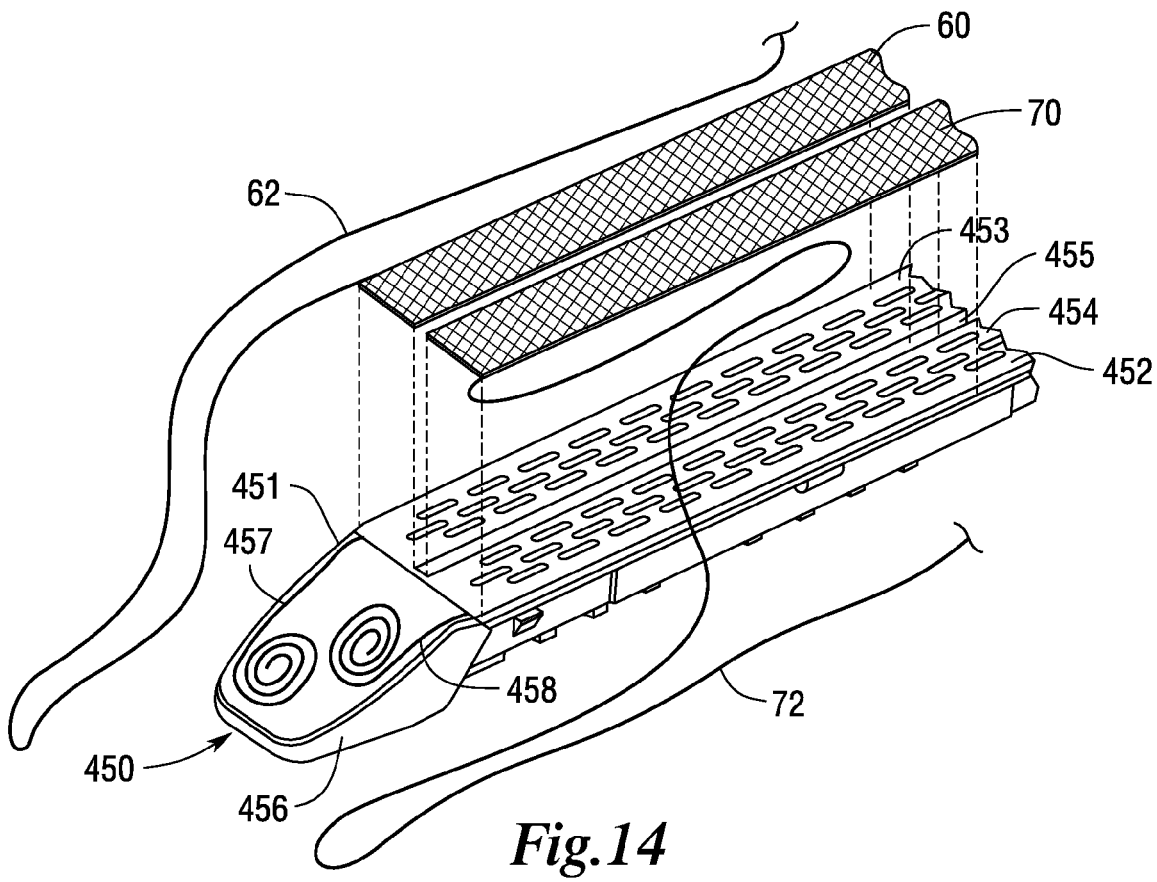
FIG. 14 is an exploded assembly view of a portion of another staple cartridge embodiment of the present invention.
Figure 15:
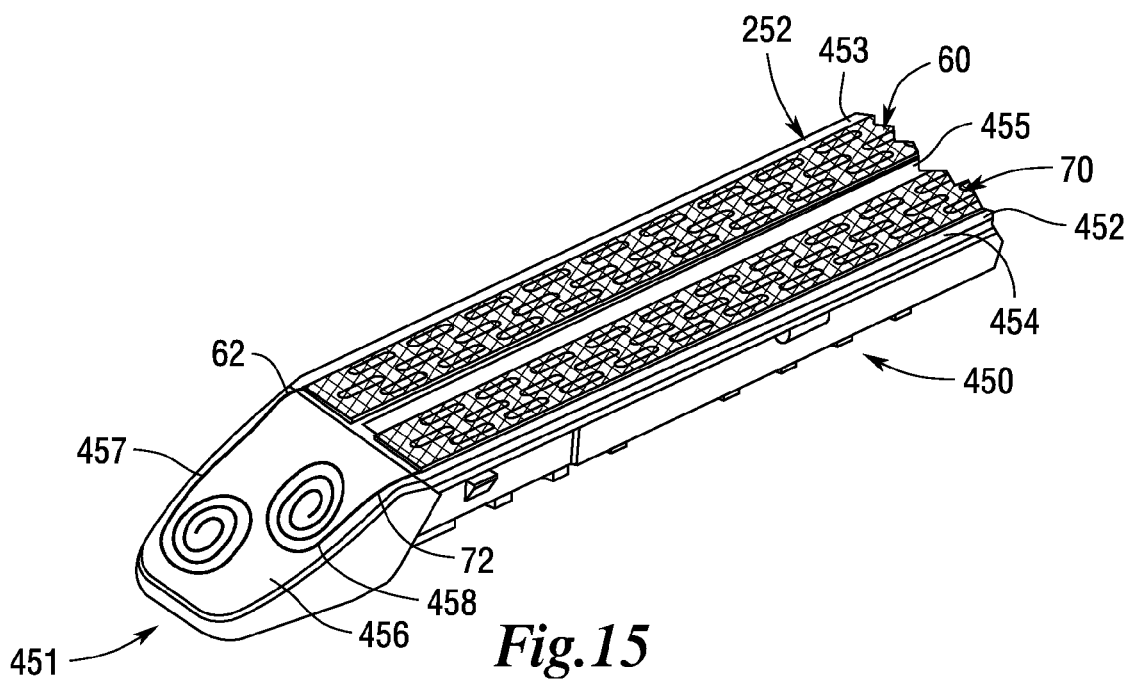
FIG. 15 is a perspective view of a portion of the staple cartridge of FIG. 14.

FIGS. 14 and 15 illustrate another cartridge embodiment 450 that is substantially identical to cartridge 50 described above, except for the differences noted below. In this embodiment for example, the cartridge 450 has a cartridge body 451 that has a cartridge deck 452 that is divided into a first deck portion 453 and a second deck portion 454 by an elongated slot 455. The first base material 60 is temporarily attached to or removably attached to or supported on the first deck portion 453. Likewise, the second base material 70 is temporarily attached to or removably attached to or supported on the second deck portion 454 in the various manners described above. In this embodiment, however, a first groove, pocket, zone or region 457 that is adapted to temporarily receive at least a portion of the first tether 62 therein is provided in the nose portion 456 of the cartridge 450. Similarly, a second groove, pocket, zone or region 458 is formed in the nose portion 456 for temporarily receiving at least a portion of the second tether 72 therein. See FIG. 15. The first groove or pocket 457 may be sized relative to the first tether 62 such that it may be pressed therein to retain it within the groove 457 while the end effector 12 is introduced to the surgical site and then is drawn out of the first groove 453 after the first base material 60 has been affixed to the tissue and the end effector 12 is withdrawn from the surgical site. Likewise, the second groove 458 may be sized relative to the second tether 72 such that it may be pressed therein to retain it within the second groove 458 while the end effector 12 is introduced to the surgical site and then is drawn out of the second groove 458 after the second base material 70 has been affixed to the tissue and the end effector 12 is withdrawn from the surgical site. In other embodiments, the first tether 62 may be temporarily retained within the first groove 457 by adhesive or friction and the second tether 72 may be temporarily retained within the second groove 458 by adhesive or friction.

Figure 16:
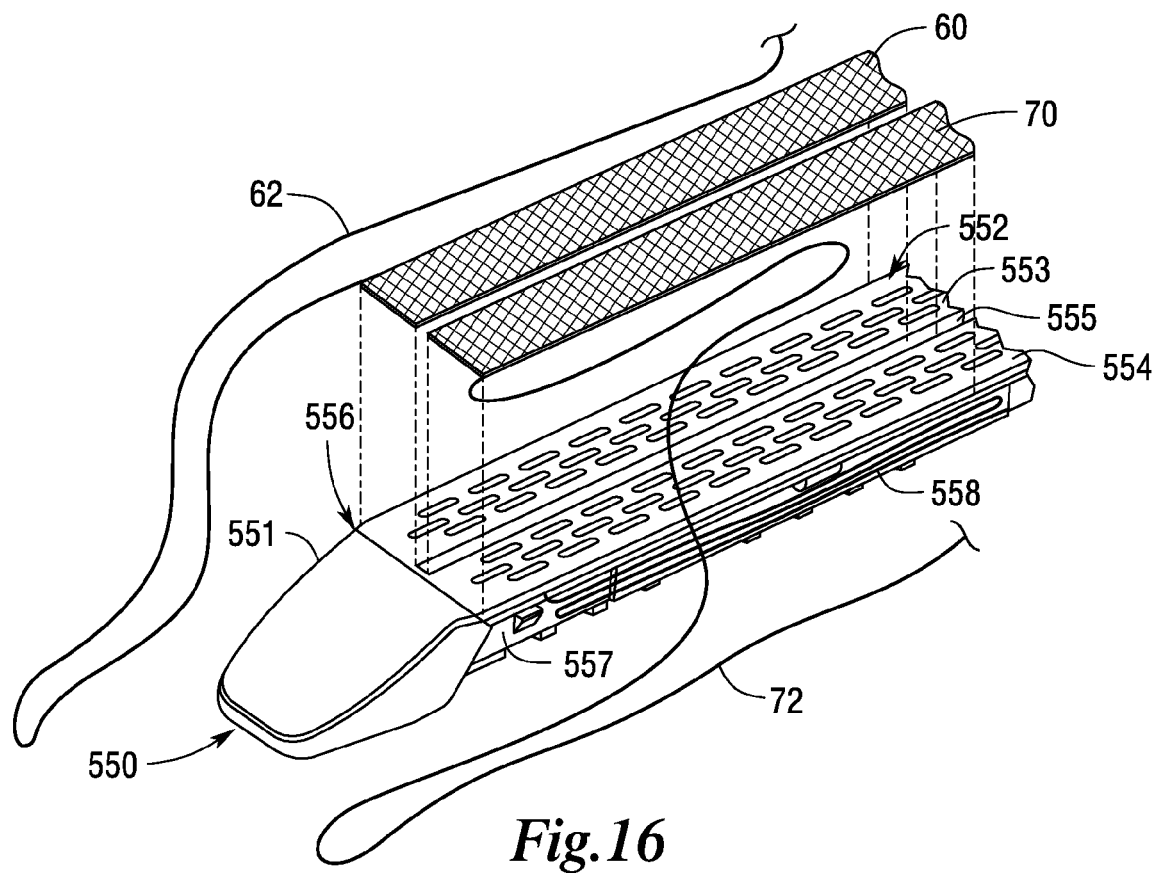
FIG. 16 is an exploded assembly view of a portion of another staple cartridge embodiment of the present invention.
Figure 17:
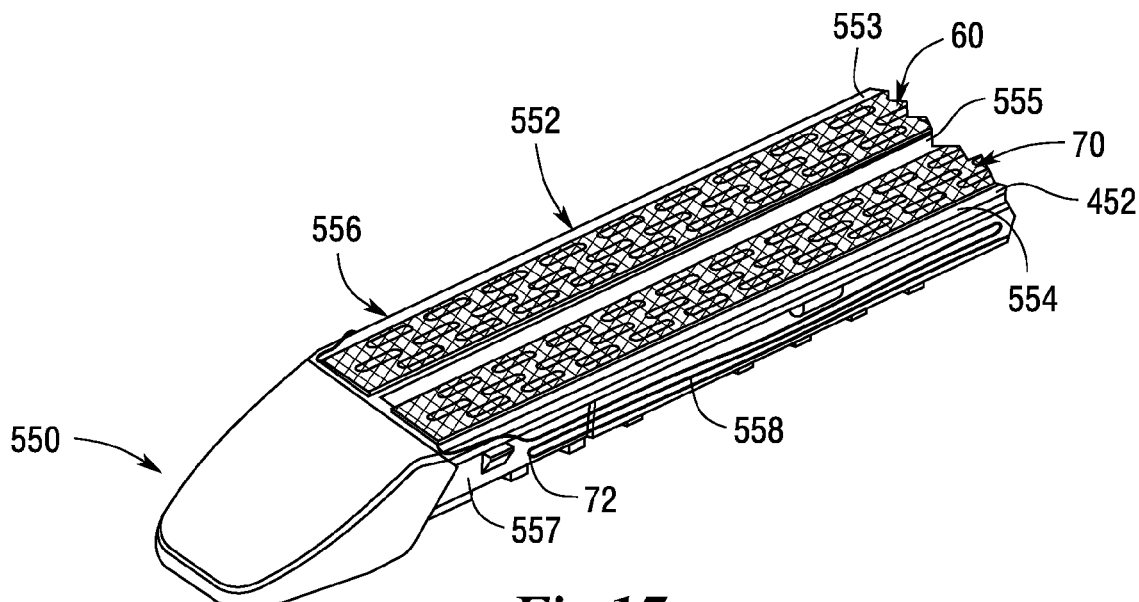
FIG. 17 is a perspective view of a portion of the staple cartridge of FIG. 16.

FIGS. 16 and 17 illustrate another cartridge embodiment 550 that is substantially identical to cartridge 50 described above, except for the differences noted below. In this embodiment for example, the cartridge 550 has a cartridge body 551 that has a cartridge deck 552 that is divided into a first deck portion 553 and a second deck portion 554 by an elongated slot 555. The first base material 60 is temporarily attached to or removably attached to or supported on the first deck portion 553. Likewise, the second base material 70 is temporarily attached to or removably attached to or supported on the second deck portion 554 in the various manners described above. In this embodiment, however, a first groove, pocket, zone or region (not shown) that is adapted to temporarily receive at least a portion of the first tether 62 therein is provided in a first lateral side portion 556 of the cartridge 550. Similarly, a second groove, pocket, zone or region 558 is formed in a second lateral side portion 557 of the cartridge 550 for temporarily receiving at least a portion of the second tether 72 therein. See FIG. 17. The first groove or pocket may be sized relative to the first tether 62 such that it may be pressed therein to retain it within that groove while the end effector 12 is introduced to the surgical site and then is drawn out of the first groove after the first base material 60 has been affixed to the tissue and the end effector 12 is withdrawn from the surgical site. Likewise, the second groove 558 may be sized relative to the second tether 72 such that it may be pressed therein to retain it within the second groove 558 while the end effector 12 is introduced to the surgical site and then is drawn out of the second groove 558 after the second base material 70 has been affixed to the tissue and the end effector 12 is withdrawn from the surgical site. In other embodiments, the first tether 62 may be temporarily retained within the first groove by adhesive or friction and the second tether 72 may be temporarily retained within the second groove 558 by adhesive or friction. In this embodiment, a sufficient amount of clearance is provided between the upstanding side walls 23, 25, of the channel (FIG. 2) and the first and second lateral side portions of the cartridge 550 to provide sufficient clearance for the first and second tethers to be pulled out of their respective grooves in the cartridge 550 or otherwise detached from the lateral sides of the cartridge 550 after the base materials 60, 70 have been stapled to the severed tissue portions and the end effector 12 is withdrawn from the surgical site.

The embodiments described above each employ first and second base materials 60 and 70. However, for those applications wherein the ability to manipulate only one portion of the divided/stapled tissue is desirable, only one base material may be employed. Thus, various embodiments of the present invention comprise at least one base material that is temporarily attached to or otherwise removably supported on the cartridge or other portion of the end effector 12 and which base material has at least one elongated tether attached thereto.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical staple cartridge comprising:
    a cartridge body operably supporting a plurality of surgical staples therein, said cartridge body comprising:
        a deck surface and first and second lateral sides; and
        a slot centrally disposed therein dividing said deck surface into a first deck portion and a second deck portion;
    a first base material segment removably retained on said first deck portion, said first base material having at least one first tether non-removably affixed thereto; and
    a second base material segment removably retained on said second deck portion, said second base material having at least one second tether non-removably affixed thereto.

2. The surgical staple cartridge of claim 1 wherein said first base material and said second base material comprise a mesh material.

3. The surgical staple cartridge of claim 1 wherein said cartridge body has a body length and wherein at least one of said at least one elongated tethers has a tether length that is at least as long as said body length.

4. The surgical staple cartridge of claim 1 wherein said first tether is removably supported on a corresponding first portion of said cartridge body and wherein said second tether is removably supported on a corresponding second portion of said cartridge body.

5. The surgical staple cartridge of claim 4 wherein each said first tether is removably supported within a corresponding first groove provided in said first portion of said cartridge body portion and wherein said second tether is removably supported within a corresponding second groove provided in said second portion of said cartridge body.

6. The surgical staple cartridge of claim 5 wherein said first groove is provided in a first lateral side portion of said cartridge body and wherein said second groove is provided in a second lateral side portion of said cartridge body.

7. The surgical staple cartridge of claim 1 wherein portions of said first and second tethers are removably supported in at least one groove is in a nose portion of said cartridge body portion.

8. A surgical end effector for use with a surgical instrument, said surgical end effector comprising:
    an elongated channel operably couplable to the surgical instrument;
    a staple cartridge having a cartridge body operably supported in said elongated channel, said cartridge body having a deck surface substantially split into a first deck portion and a second deck portion by a longitudinal slot extending therebetween, said cartridge body operably supporting a first plurality of unformed staples therein corresponding to said first deck portion and a second plurality of unformed staples corresponding to said second deck portion;
    a tissue cutting member operably supported in said cartridge body for axial advancement in said longitudinal slot upon application of a cutting actuation motion thereto by the surgical instrument;
    an anvil supported for movable travel toward and away from said deck surface in response to opening and closing motions applied thereto by the surgical instrument;
    a first base material removably supported on said first deck portion;
    at least one first tether non-removably attached to said first base material;
    a second base material removably supported on said second deck portion; and
    at least one second tether non-removably attached to said second base material.

* * * * *